(12) United States Patent
Munster et al.

(10) Patent No.: US 11,918,770 B2
(45) Date of Patent: *Mar. 5, 2024

(54) IMPLANTS FOR LOCALIZED DRUG DELIVERY AND METHODS OF USE THEREOF

(71) Applicant: The Regents of the University of California, Oakland, CA (US)

(72) Inventors: Pamela Munster, Hillsborough, CA (US); Jim Kiriakis, Corte Madera, CA (US); Hani Sbitany, San Francisco, CA (US); Scott Thomas, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/666,138

(22) Filed: Feb. 7, 2022

(65) Prior Publication Data

US 2022/0184362 A1 Jun. 16, 2022

Related U.S. Application Data

(63) Continuation of application No. 16/273,760, filed on Feb. 12, 2019, now Pat. No. 11,324,935, which is a
(Continued)

(51) Int. Cl.
*A61M 31/00* (2006.01)
*A61K 9/00* (2006.01)
(Continued)

(52) U.S. Cl.
CPC ......... *A61M 31/002* (2013.01); *A61K 9/0004* (2013.01); *A61K 9/0024* (2013.01);
(Continued)

(58) Field of Classification Search
CPC ........... A61B 2018/00547; A61B 7/00; A61M 37/0069; A61M 31/002; A61M 2205/04;
(Continued)

(56) References Cited

U.S. PATENT DOCUMENTS 3,279,996 A 10/1966 Long, Jr. et al.
3,755,042 A 8/1973 Robertson et al.
(Continued)

FOREIGN PATENT DOCUMENTS

CN 101896221 11/2010
CN 107753418 6/2018
(Continued)

OTHER PUBLICATIONS

Jakawich (2012) "A New Twist on Treating Chronic Bladder Pain", Pain Research Forum, 4 pages.
(Continued)

*Primary Examiner* — Kevin C Sirmons
*Assistant Examiner* — Alexandra Lalonde
(74) *Attorney, Agent, or Firm* — Edward J. Baba; Bozicevic, Field & Francis LLP

(57) ABSTRACT

Provided herein is an implant for delivering a hydrophobic active agent to a target tissue. The implant may include a scaffold defining a first surface and a second surface opposite the first surface, wherein the scaffold is substantially impermeable to a hydrophobic active agent, and a silicone tubing having a wall permeable to the active agent, wherein a first length of the silicone tubing is affixed to the first surface of the scaffold, wherein the two ends of the silicone tubing extend from the first surface, and wherein a path outlined by a second length of the tubing within the first length is circuitous. Also provided is a method of using the
(Continued)

implant to locally deliver a hydrophobic active agent to a target tissue, and kits that find use in performing the present method.

22 Claims, 20 Drawing Sheets

Related U.S. Application Data continuation of application No. 15/502,742, filed as application No. PCT/US2015/045687 on Aug. 18, 2015, now Pat. No. 10,912,933.

(60) Provisional application No. 62/039,302, filed on Aug. 19, 2014.

(51) Int. Cl.
| | | |
|---|---|---|
| *A61K 31/56* | (2006.01) | |
| *A61K 31/565* | (2006.01) | |
| *A61L 27/18* | (2006.01) | |
| *A61L 27/54* | (2006.01) | |

(52) U.S. Cl.
CPC .......... *A61K 9/0041* (2013.01); *A61K 9/0092* (2013.01); *A61K 31/56* (2013.01); *A61K 31/565* (2013.01); *A61L 27/18* (2013.01); *A61L 27/54* (2013.01)

(58) Field of Classification Search
CPC .......... A61M 2210/14; A61M 2210/16; A61M 2202/06; A61M 31/00; A61M 31/007; A61M 37/00; A61K 9/0004; A61K 9/0024; A61K 9/0041; A61K 9/0092; A61K 9/0002; A61K 9/0019; A61K 9/0012; A61K 9/0034; A61K 31/56; A61K 31/565; A61D 7/00; A61L 27/18; A61L 27/54; A61L 27/14; A61L 27/50; A61F 2/02; A61F 2230/0065; A61F 2230/0091; A61F 2250/0067; A61F 2250/0078
See application file for complete search history.

(56) References Cited

U.S. PATENT DOCUMENTS

| | | | |
|---|---|---|---|
| 4,012,497 A | 3/1977 | Schopflin | |
| 4,144,317 A | 3/1979 | Higuchi et al. | |
| 4,304,765 A | 12/1981 | Shell et al. | |
| 4,482,053 A | 11/1984 | Alpern et al. | |
| 4,668,506 A | 5/1987 | Bawa | |
| 4,750,619 A | 6/1988 | Cohen et al. | |
| 4,959,217 A | 9/1990 | Sanders et al. | |
| 5,824,074 A | 10/1998 | Koch | |
| 6,071,305 A | 6/2000 | Brown et al. | |
| 6,117,441 A | 9/2000 | Moo-Young et al. | |
| 6,196,993 B1 | 3/2001 | Cohan et al. | |
| 6,331,313 B1 | 12/2001 | Wong et al. | |
| 6,358,276 B1 | 3/2002 | Edwin | |
| 6,623,519 B2 | 9/2003 | Edwin et al. | |
| 6,881,220 B2 | 4/2005 | Edwin et al. | |
| 8,182,464 B2 | 5/2012 | Lee et al. | |
| 8,795,711 B2 | 8/2014 | De Juan, Jr. et al. | |
| 8,801,694 B2 | 8/2014 | Lee et al. | |
| 8,999,945 B2 | 4/2015 | Shemi | |
| 9,005,649 B2 | 4/2015 | Ho et al. | |
| 9,107,816 B2 | 8/2015 | Lee et al. | |
| 9,345,867 B2 | 5/2016 | Browing | |
| 9,561,353 B2 | 2/2017 | Lee et al. | |
| 9,586,035 B2 | 3/2017 | Cima et al. | |
| 10,532,132 B2 | 1/2020 | Tobias et al. | |
| 2002/0049426 A1 | 4/2002 | Butler et al. | |
| 2003/0147936 A1 | 8/2003 | Sahadevan | |
| 2005/0153923 A1* | 7/2005 | Kinch .................. | C07K 14/715 424/155.1 |
| 2005/0187612 A1 | 8/2005 | Edwin | |
| 2005/0268573 A1 | 12/2005 | Yan | |
| 2007/0088336 A1 | 4/2007 | Dalton | |
| 2008/0286205 A1* | 11/2008 | Lennernas .......... | A61K 9/1647 424/9.4 |
| 2009/0104243 A1* | 4/2009 | Utkhede ............... | A61F 9/0017 424/423 |
| 2009/0149833 A1 | 6/2009 | Cima et al. | |
| 2009/0149838 A1 | 6/2009 | Cassada | |
| 2009/0311304 A1 | 12/2009 | Borck et al. | |
| 2010/0003297 A1 | 1/2010 | Tobias et al. | |
| 2010/0133133 A1 | 6/2010 | Hamas | |
| 2010/0331760 A1 | 12/2010 | Atanasoska et al. | |
| 2011/0229457 A1* | 9/2011 | Kloke ..................... | A61P 31/14 514/777 |
| 2012/0083751 A1 | 4/2012 | Dalton | |
| 2012/0093262 A1 | 4/2012 | Seo et al. | |
| 2012/0130300 A1 | 5/2012 | Staychansky et al. | |
| 2012/0203203 A1 | 8/2012 | Lee et al. | |
| 2013/0325121 A1 | 12/2013 | Whatley et al. | |
| 2015/0045687 A1 | 2/2015 | Nakai et al. | |
| 2015/0080847 A1 | 3/2015 | Cima et al. | |
| 2015/0182516 A1 | 7/2015 | Giesing | |
| 2015/0208982 A1 | 7/2015 | Ho et al. | |
| 2016/0051477 A1 | 2/2016 | Gopinathan | |
| 2017/0157360 A1 | 6/2017 | Cima et al. | |
| 2017/0224970 A1 | 8/2017 | Munster et al. | |
| 2018/0042549 A1 | 2/2018 | Ho et al. | |
| 2018/0140748 A1 | 5/2018 | Lee et al. | |
| 2018/0333509 A1 | 11/2018 | Aston et al. | |
| 2019/0184145 A1 | 6/2019 | Munster | |

FOREIGN PATENT DOCUMENTS

| | | | | |
|---|---|---|---|---|
| EP | 2475354 | | 7/2012 | |
| GB | 2154138 | | 9/1985 | |
| JP | 2011-505988 | | 3/2011 | |
| JP | 2013213020 | | 10/2013 | |
| JP | 2014509315 | | 4/2014 | |
| WO | 9823228 | | 6/1998 | |
| WO | 0018327 | | 4/2000 | |
| WO | 2005039537 | | 5/2005 | |
| WO | 2010065358 | | 6/2010 | |
| WO | 2012047931 | | 4/2012 | |
| WO | 2012170578 | | 12/2012 | |
| WO | WO-2012170578 A1 * | 12/2012 | .......... | A61K 31/675 |
| WO | 2013148682 | | 10/2013 | |
| WO | 2014047221 | | 3/2014 | |
| WO | 2016028774 | | 2/2016 | |
| WO | 2016149561 | | 9/2016 | |

OTHER PUBLICATIONS

Rahimi et al (2009) "Silicone Polymers in Controlled Drug Delivery Systems: A Review", Iranian Polymer Journal, 18(4), 279-295.
Reilly et al (2004) "Silicones as a Material of Choice for Drug Delivery Applications", 31st Annual Meeting and Exposition of the Controlled Release Society, 10 pages.
Reilly et al (2006) "Silicones for Drug-Delivery Applications", MDDI, 9 pages.
European Search Report dated Jan. 23, 2018 from EP 15833347.6.
International Search Report dated Nov. 24, 2015 from PCT/US2015/045687.
"U.S. Appl. No. 15/502,742 Office Action dated Aug. 15, 2019."
"U.S. Appl. No. 16/273,760 Office Action dated May 28, 2019."

* cited by examiner

Section A-A'

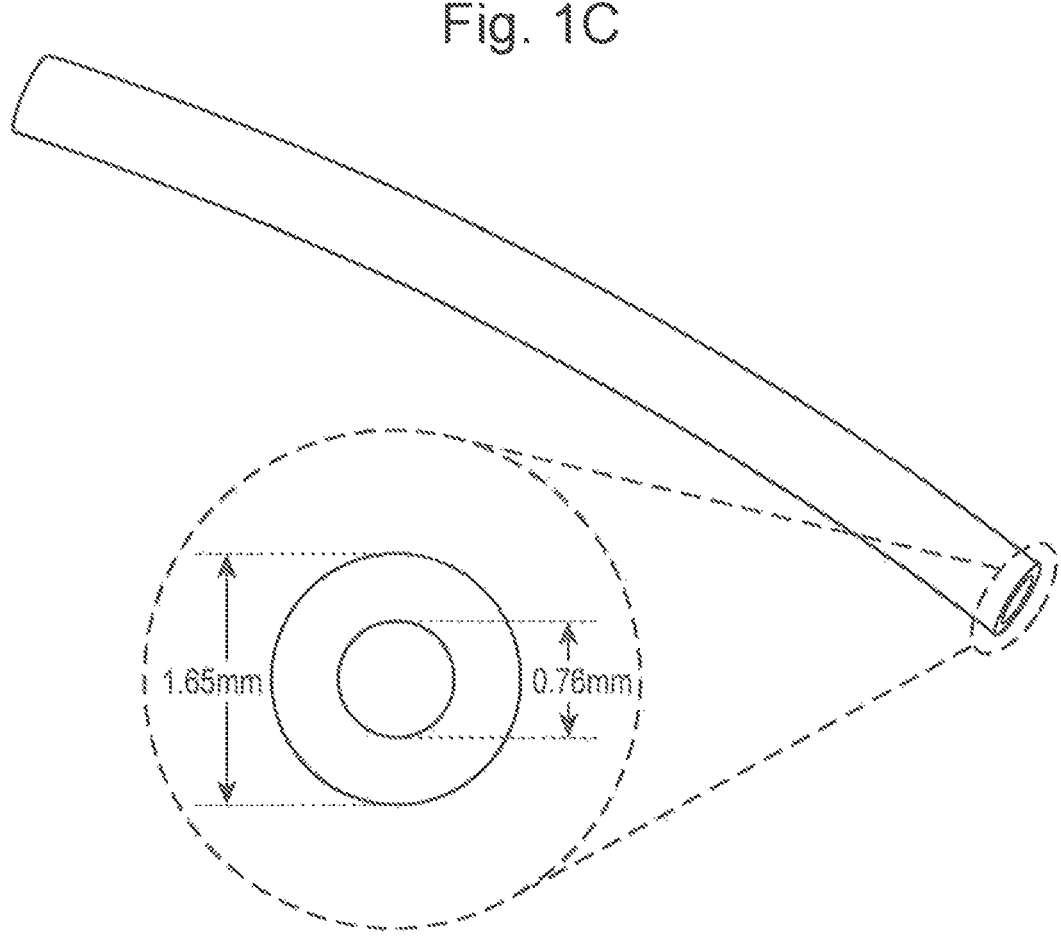

Section B-B'

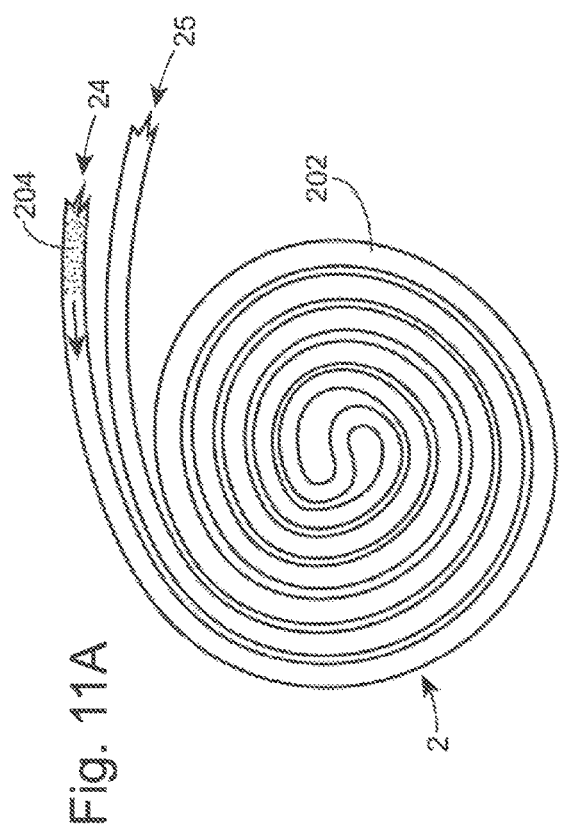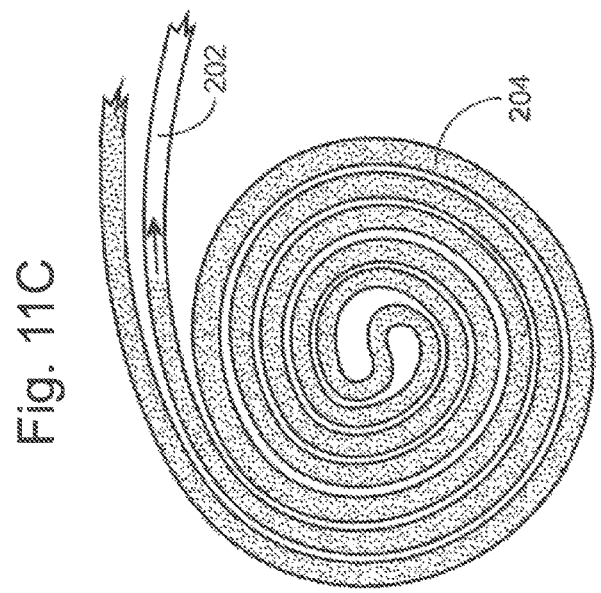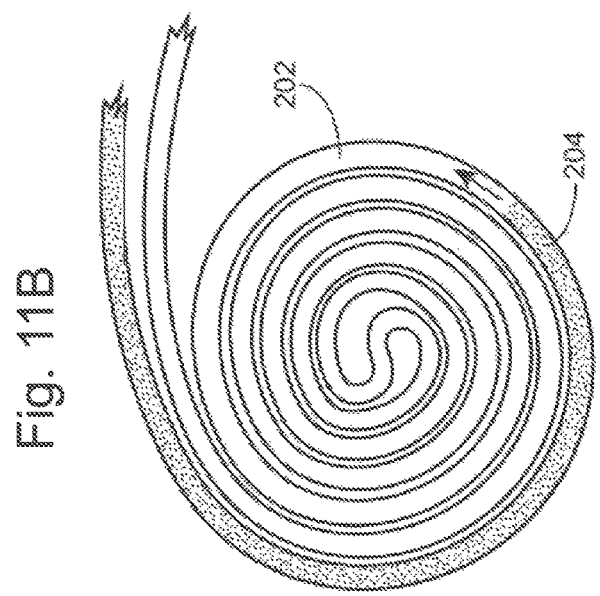

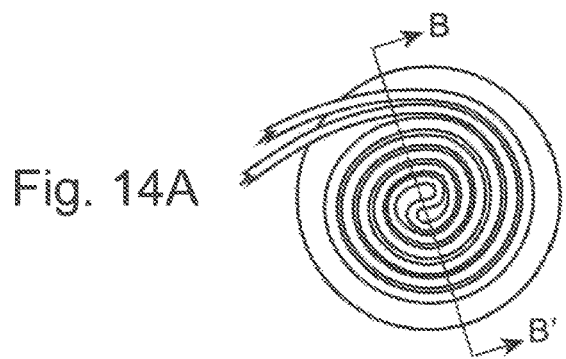
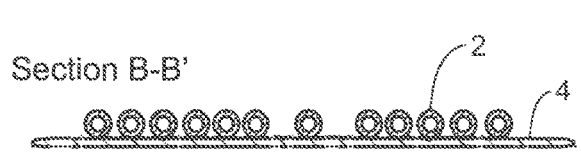
Fig. 14A
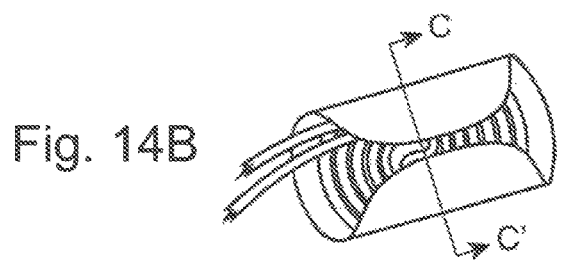
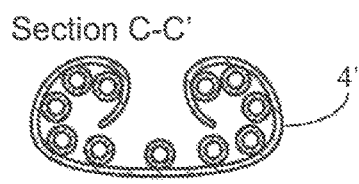
Fig. 14B
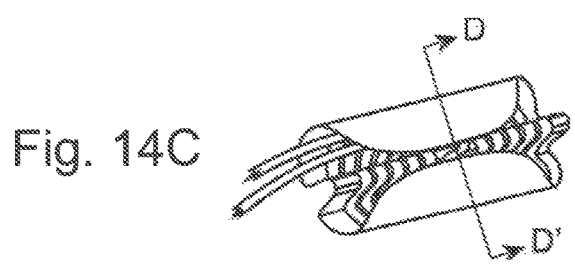
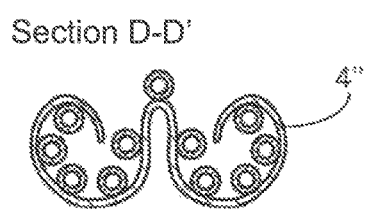
Fig. 14C
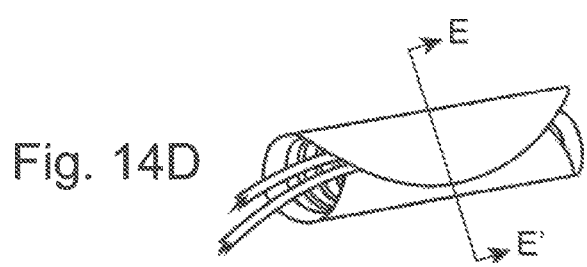
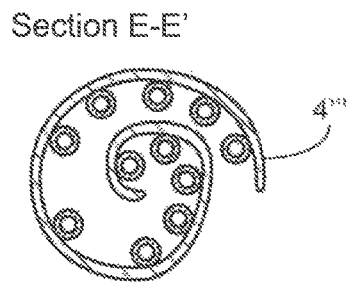
Fig. 14D

FIG. 22

Table 1

Plasma

| Week | Replicate | Fulvestrant (nM) |
|---|---|---|
| Week 1 | A | < 4 |
|  | B | < 4 |
|  | C | < 4 |
|  | D | < 4 |
| Week 2 | A | < 4 |
|  | B | < 4 |
|  | C | < 4 |
|  | D | < 4 |
| Week 3 | A | < 4 |
|  | B | < 4 |
|  | C | < 4 |
|  | D | < 4 |
| Week 4 | A | < 4 |
|  | B | < 4 |
|  | C | < 4 |
|  | D | 4.22 |
| Week 6 | A | < 4 |
|  | B | < 4 |
|  | C | < 4 |
|  | D | < 4 |
| Week 9 | A | < 4 |
|  | B | < 4 |
|  | C | < 4 |
|  | D | < 4 |

IMPLANTS FOR LOCALIZED DRUG DELIVERY AND METHODS OF USE THEREOF

CROSS-REFERENCE TO RELATED APPLICATIONS

This application is a continuation of U.S. application Ser. No. 16/273,760, filed on Feb. 12, 2019, which is a continuation of U.S. application Ser. No. 15/502,742, filed on Feb. 8, 2017, which is a 371 of International Application Serial No. PCT/US2015/045687, filed on Aug. 18, 2015, which claims the benefit of U.S. Provisional Patent Application No. 62/039,302, filed Aug. 19, 2014, which application is incorporated herein by reference in its entirety.

BACKGROUND

Reservoir-based systems for drug delivery provide a way to deliver drugs to a patient using passive or active mechanisms, and include oral, dermal and implantable systems. Passive systems utilize diffusion, osmotic potential, or concentration gradients as their driving forces, while active systems include mechanical pumping, electrolysis, and other actuation methods. Reservoir-based implants can be used for both systemic and targeted drug delivery applications.

Breast cancer is the most common cancer diagnosed in US women, and the second leading cause of death from cancer in US women. Over 200,000 women are diagnosed with breast cancer each year in the United States, and 5-10% of these are related to hereditary mutations such as the BRCA 1 and 2 gene mutations. The treatments for these women include surgical removal of the breasts or systemic pharmacologic estrogen withdrawal, such as through systemically delivered antiestrogens.

The burden of suffering from prostate cancer in the United States is significant. In 2009, approximately 192,000 men were diagnosed with prostate cancer, and 27,000 men were expected to die from this disease. Approximately 2.2 million living American men have been diagnosed with prostate cancer, and some are living with metastatic disease, a painful and functionally limiting stage of the disease. Prostate cancer is by far the most commonly diagnosed cancer among American men and remains the second leading cause of cancer death in men. Hormonal therapy of prostate cancer includes a wide variety of treatments designed to affect cells whose normal functioning depends on androgens, which include testosterone and dihydrotestosterone, among others. Prostate cancer cells are generally very susceptible to treatments that lower androgen levels or affect the normal action of these hormones.

SUMMARY

Provided herein is an implant for delivering a hydrophobic active agent to a target tissue. The implant may include a scaffold defining a first surface and a second surface opposite the first surface, wherein the scaffold is substantially impermeable to a hydrophobic active agent, and a silicone tubing having a wall permeable to the active agent, wherein a length of the silicone tubing is affixed to the first surface of the scaffold, wherein the two ends of the silicone tubing extend from the first surface, and wherein a path outlined by a second length of the tubing within the first length is circuitous. Also provided is a method of using the implant to locally deliver a hydrophobic active agent to a target tissue, and kits that find use in performing the present method. In some embodiments, the silicone tubing is SILASTIC tubing.

In any embodiment, the implant may define a first, second and third orthogonal dimensions, and wherein the length of the silicon tubing is longer than the longest dimension of the first, second and third orthogonal dimensions.

In any embodiment, the circuitous path may include one or more switchbacks on the first surface of the scaffold. In some embodiments, the circuitous path includes a spiral pattern.

In any embodiment, the first length of the silicone tubing may overlie 30% or more of the first surface of the scaffold.

In any embodiment, an amount of liquid introduced into the implant from the first end of the silicone tubing under sufficient pressure advances through the tubing to reach the second end when a volume of liquid in the implant approximately equal to an internal volume of the silicone tubing between the first and second ends is displaced by the applied pressure.

In any embodiment, the scaffold is substantially planar.

In any embodiment, the scaffold may be a polymeric scaffold.

In any embodiment, the silicone tubing includes an amount of the active agent sufficient to deliver a therapeutically effective amount of the active agent to the target tissue. In some embodiments, the wall of the silicone tubing includes an amount of the active agent sufficient to deliver a therapeutically effective amount of the active agent to the target tissue. In some cases, the silicone tubing includes the active agent in an amount sufficient to achieve sustained delivery of the active agent into the target tissue.

In any embodiment, the active agent is a steroid. In some cases, the steroid is cholesterol, estradiol, progesterone, testosterone, or derivatives or synthetic analogs thereof. In some embodiments, the steroid is an anti-estrogen. In some cases, the anti-estrogen is fulvestrant.

In any embodiment, the implant may include one of more suture tabs.

In any embodiment, the implant may further include one or more fill ports attached to the first and second ends of the silicone tubing. In some cases, the implant includes a fill port containing a first chamber in fluid communication at the fill port with the first end of the silicone tubing, and a second chamber in fluid communication at the fill port with the second end of the silicone tubing. In some embodiments, the fill port includes an imageable backing. In certain embodiments, the fill port includes one or more suture tabs.

Also provided herein is a method of delivering a hydrophobic active agent to a target tissue in a subject, the method including the step of implanting an implant of any of the embodiments disclosed above in a target tissue, in a manner sufficient to locally deliver a therapeutically effective amount of a hydrophobic active agent into the target tissue, wherein the implanted implant includes the active agent. In some embodiments, the hydrophobic active agent is substantially undetectable in the non-target tissue after implanting the implant. In certain embodiments, the hydrophobic active agent is substantially undetectable in a non-target tissue for one week or more after implanting the implant. In some cases, the non-target tissue includes circulating blood. In certain embodiments, the subject is a subject diagnosed as having or being predisposed to having cancer. In certain cases, the target tissue comprises breast, prostate, uterine, brain, skin, ovarian, gastrointestinal, bladder, muscle, liver, kidney or pancreatic tissue. In some embodiments, the implanting includes changing the configuration of the implant into a delivery configuration, positioning the implant in the delivery configuration into the tissue, and changing the configuration of the positioned implant into a functional configuration. In some cases, the silicone tubing in the implanted implant includes the hydrophobic active agent in dry or liquid form. In some cases, the hydrophobic active agent in liquid form is in an organic solvent.

In any embodiment, the method may further include loading the silicone tubing with the hydrophobic active agent. In some cases, the loading includes introducing a solution containing the hydrophobic active agent into a first end of the silicone tubing, and applying pressure to the solution in the tubing in a manner sufficient to advance the solution through the silicone tubing to the second end. In some cases, the loading is performed after implanting. In some cases, the method includes loading the silicone tubing with a first hydrophobic active agent before implanting, and loading the silicone tubing with a second hydrophobic active agent after implanting.

In any embodiment, the method may further include removing the hydrophobic active agent from the silicone tubing after implanting.

Also provided herein is an implant for delivering a hydrophobic active agent to a target tissue, the implant containing a depot for holding the hydrophobic active agent, wherein the depot includes a silicone tubing defining a first end and a second end distal to the first end, wherein the silicone tubing includes a wall permeable to the active agent, and the silicone tubing includes a switchback, wherein the switchback and the first end define a first length of the tubing, and the switchback and the second end define a second length of the tubing, and wherein the first and second lengths are intertwined with each other substantially along their respective lengths. In some cases, an amount of liquid introduced into the implant from the first end under sufficient pressure advances through the tubing to reach the second end when a volume of liquid in the implant approximately equal to an internal volume of the silicone tubing between the first and second ends is displaced by the applied pressure.

Kits that include an implant of the present disclosure and that find use in implementing the present method are also provided.

BRIEF DESCRIPTION OF THE FIGURES

The skilled artisan will understand that the drawings, described below, are for illustration purposes only. The drawings are not intended to limit the scope of the present teachings in any way.

FIGS. 1A-C are illustrations showing an implant for active agent delivery, according to embodiments of the present disclosure.

FIGS. 11A-C are schematic illustrations showing a method of loading an implant for active agent delivery, according to embodiments of the present disclosure.

FIGS. 14A-D are illustrations showing various configurations of an implant for active agent delivery, according to embodiments of the present disclosure.

FIG. 22 shows Table 1, showing amounts of fulvestrant measured in blood from mice implanted with a fulvestrant-loaded implant in mammary tissue, according to embodiments of the present disclosure.

DEFINITIONS

Figure 1A:
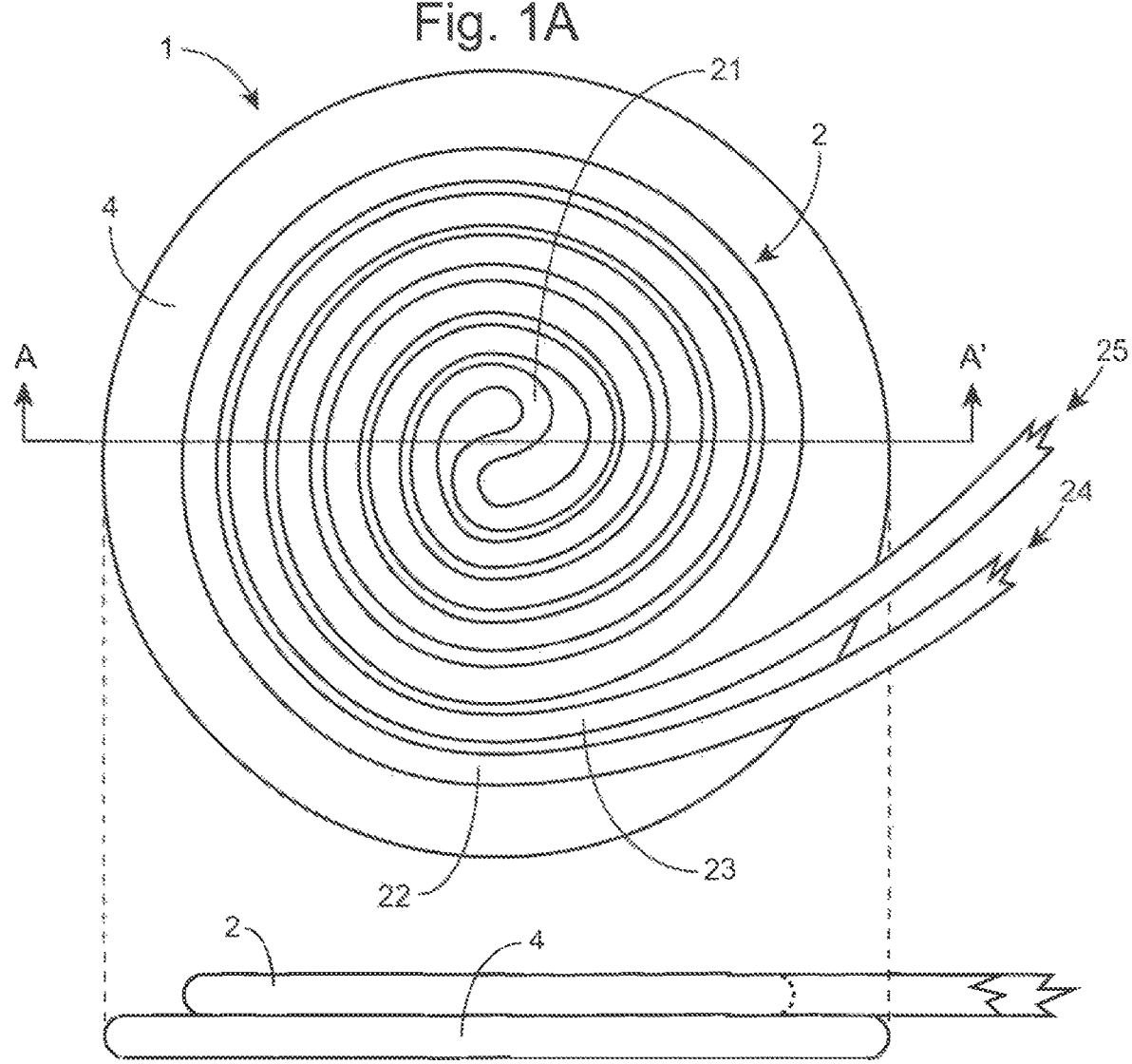

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

"Subject" refers to any animal, e.g., a mouse, rat, goat, dog, pig, monkey, non-human primate, or a human.

"Biocompatible," as used herein, refers to a property of a material that allows for prolonged contact with a tissue in a subject without causing toxicity or significant damage.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

"Active agent" and "drug" are used interchangeably to refer to any chemical compound that can have a therapeutic and/or preventive effect for a disease when suitably administered to a subject.

"Therapeutically effective amount" refers to an amount effective, at dosages and for periods of time necessary, to achieve the desired therapeutic result.

"Target," as used in reference to a tissue or site, refers to a tissue or location within a subject's body to which an active agent is, or is intended to be, delivered by an implant of the present disclosure. The target tissue can include pathological tissue, e.g., cancerous tissue, that is to be treated by the active agent, or can include tissue where occurrence or recurrence of pathology, e.g., cancer, is to be prevented or delayed. A "non-target tissue" may refer to any tissue that is not the intended target for delivering an active agent using the implant. In some cases, the non-target tissue is a tissue that is adjacent the target tissue. In some cases, the non-target tissue includes a systemically circulating tissue, such as blood.

"Local," as used in reference to delivery of an active agent to a target tissue, is meant to characterize the distribution of the active agent in the body of a subject preferentially to the target tissue compared to non-target tissue. In some cases, the local delivery of the active agent to the target tissue includes the active agent being substantially absent from a non-target tissue.

"Hydrophobic" and "lipophilic" are used interchangeably to refer to a property of a compound to dissolve more readily in an organic solvent (e.g., dimethylsulfoxide (DMSO), ethanol, methanol, dimethylformamide (DMF), octanol, castor oil, etc.) compared to an aqueous solution at ambient temperature. The hydrophobicity or lipophilicity of the hydrophobic compound, as defined by the distribution coefficient (log D) between water and octanol, may be 4 or higher.

"Tubing," as used herein refers to an elongated structure having a cylindrical wall defining an interior space. A tubing can have a substantially constant inner diameter along the length of the tubing that forms the implant. The length of the elongated structure may be longer than the width by a factor of 20 or more.

An "end," as used in reference to an end of a tubing, is meant to indicate an extremity or an extreme portion of the tubing. The end of a tubing does not necessarily refer to a physical termination of the tubing, although the end of the tubing may in some cases coincide with a physical break in the tubing, depending on context.

The "internal volume," as used in reference to a tubing, refers to the volume of the space in the tubing bound by the internal wall.

"Remote," as used herein, refers to a physically distinct location relative to a component of an implant of the present disclosure that is, or is to be, implanted at a target tissue to which an active agent is to be delivered by the implant.

"Outline," as used in reference to an outline of an elongated structure, refers to a line representing the elongated structure formed by reducing the structure to only its longitudinal dimension, e.g., by skeletonizing the profile of the elongated structure at all points along the structure.

"Circuitous," as used herein, refers to a path outlined by a length of tubing not being a straight path. The circuitous outline may form a pattern in two or three dimensions. In some cases, a circuitous path outlined by a length of tubing may change directions by 180° or more, e.g., 270° or more, 360° or more, 540° or more, including 720° or more between two points along the length.

"Orthogonal dimensions," as used herein, refers to the three independent axes of three dimensional space, commonly referred to as the x-, y- and z-axes.

A "switchback," as used in reference to a length of tubing, refers to a pattern formed by the length of tubing where the path along the tubing undergoes a turn of about 180° within a short portion of the length of tubing. A switchback in a tubing results in the two sections of the tubing adjacent the switchback being substantially parallel to each other. The curvature of the switchback, may be substantially higher in magnitude than the curvature of the two sections of the tubing adjacent the switchback (i.e., is a local maximum or minimum of curvature), measured in the plane of the two sections of the tubing.

"Unidirectional," as used in reference to localized delivery of an active agent to a target tissue, is meant to indicate that the diffusion or migration of the active agent through the tissue is biased in favor of a first direction relative to a surface, e.g., a surface of the scaffold on which a silicone tubing is affixed, compared to a second direction relative to the surface that is opposite from the first direction.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that embodiments of the present disclosure are not limited in its application to the details of construction, the arrangements of components, category selections, weightings, pre-determined signal limits, or the steps set forth in the description or drawings herein. The present disclosure may encompass other embodiments and may be practiced or be carried out in many different ways.

DETAILED DESCRIPTION

As summarized above, the present disclosure provides an implant for delivering a hydrophobic active agent to a target tissue, the implant including a scaffold defining a first surface and a second surface opposite the first surface, wherein the scaffold is substantially impermeable to a hydrophobic active agent, and a silicone tubing having wall permeable to the active agent, wherein a length of the silicone tubing is affixed to the first surface of the scaffold, wherein the two ends of the silicone tubing extend from the first surface, and wherein a path outlined by a second length of the tubing within the first length is circuitous.

The silicone tubing of the present implant is permeable to a hydrophobic active agent, e.g., an anti-estrogen or a steroid, and serves as a depot of the hydrophobic active agent when the implant is implanted in a subject. The silicone tubing can be shaped such that the path outlined by the tubing forms a circuitous pattern, e.g., on the surface of a scaffold, as described further below. Once implanted, a hydrophobic active agent that is loaded in the silicone tubing elutes from the silicone tubing into the surrounding tissue. Thus, the implant of the present disclosure can provide sustained, long-term delivery of the hydrophobic active agent without the silicone tubing being connected to a chamber or reservoir at the target tissue to hold, e.g., a solution containing the hydrophobic active agent. In addition, the use of a single tubing as both the conduit for loading the implant with various solutions as well as the depot for the active agent, solution exchange is facilitated as the tubing provides a circular flow of solution, entering the implant from one end of the tubing and exiting from the other end.

An implant of the present disclosure provides for localized delivery of the hydrophobic active agent from the silicone tubing for treatment of the target tissue, while reducing the spread of the hydrophobic active agent to non-target tissue and hence reducing systemic side effects and/or toxicity. This can be achieved by attaching the silicone tubing to a scaffold, e.g., a backing, which serves as a barrier for diffusion of the hydrophobic active agent. Thus, the present implant can provide unidirectional, localized and sustained release of the hydrophobic active agent at the site of implantation.

Implants for Delivering an Active Agent

Figure 1B:
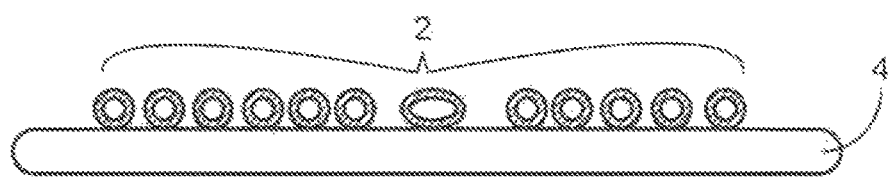

An embodiment of the implant for delivering an active agent to a target tissue is shown in FIGS. 1A-C. The implant 1 includes a length of silicone tubing 2 affixed to a surface of a scaffold 4. The tubing contains a central switchback 21 such that a first length of the tubing 22 lies alongside a second length of the tubing 23. The first and second lengths of the tubing together form a spiral pattern originating from the location of the central switchback. A regular spiral pattern allows for the tubing to be distributed at regular intervals over the surface of the scaffold between the location of the central switchback and the length of tubing at the outer most edge of the spiral pattern. The first length of the tubing defines a first end 24 distal to the second length, and the second length of the tubing defines a second end 25 distal to the first length. The first and second ends of the tubing extend out from the implant. The tubing serves as a depot for holding an active agent, e.g., a drug, in the implant, from which the drug elutes into the surrounding tissue.

The silicone tubing may be Silastic® Rx 50 Tubing, as Seen in FIG. 1C. This Tubing is a biomedical grade silicone polymer approved by the U.S. Food and Drug Administration (FDA) as a medical device safe for implantation in the human body. The tubing has an inner diameter of 0.76 mm, and an outer diameter of 1.65 mm.

The scaffold 4 can be a substantially circular shape and can be sized to the desired diameter to cover the target tissue. The scaffold can extend beyond the spiral pattern formed by the silicone tubing. The scaffold 4 is made of any suitable material that is substantially impermeable to the active agent being eluted from the silicone tubing 2, to prevent diffusion of the active agent in the direction of the scaffold from the tubing, and achieve unidirectional delivery of the active agent from the implant (see also, FIG. 12).

Figure 2A:
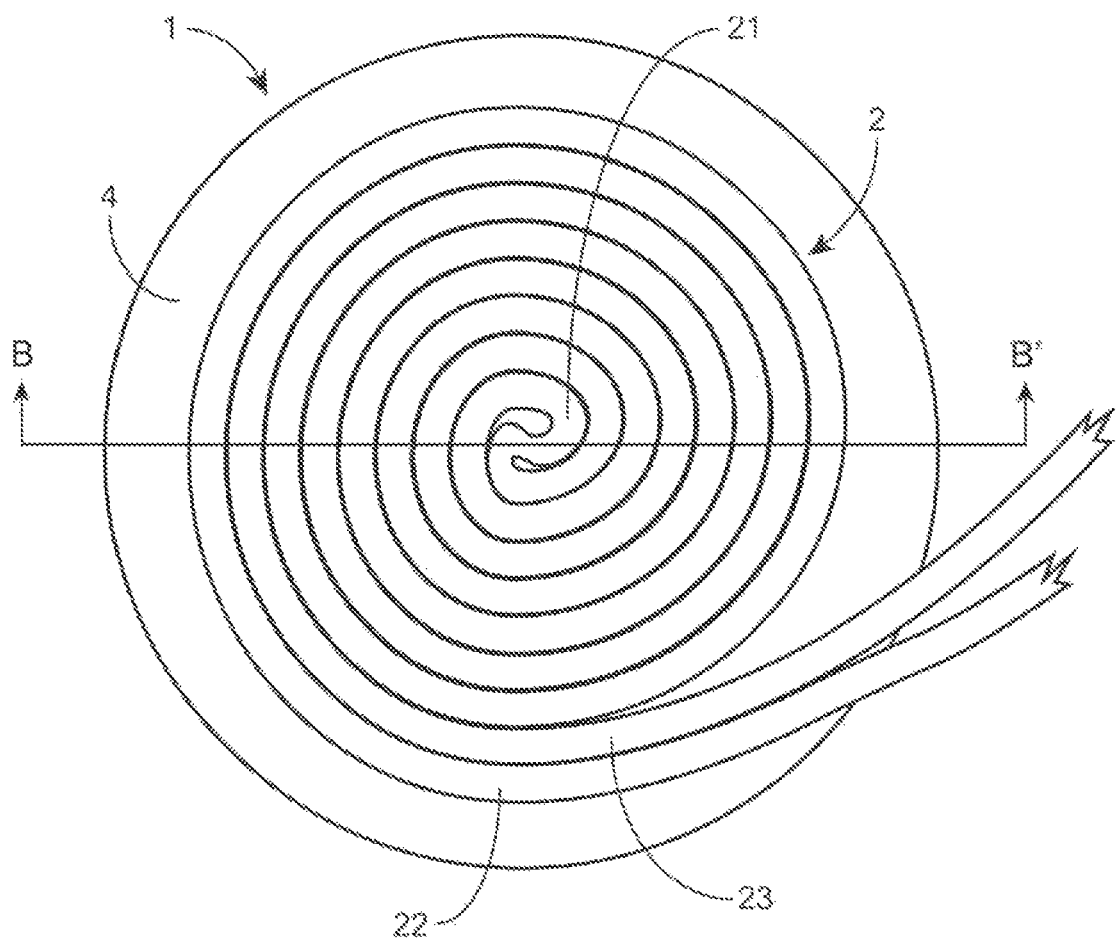
FIGS. 2A-B are illustrations showing an implant for active agent delivery, according to embodiments of the present disclosure.
Figure 2B:
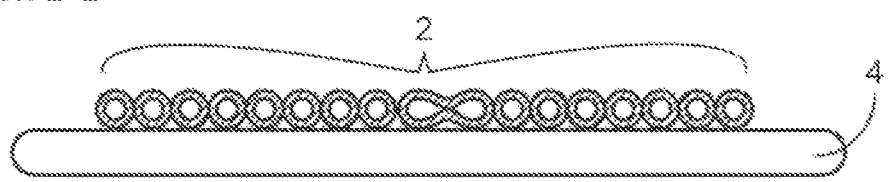
Figure 3:
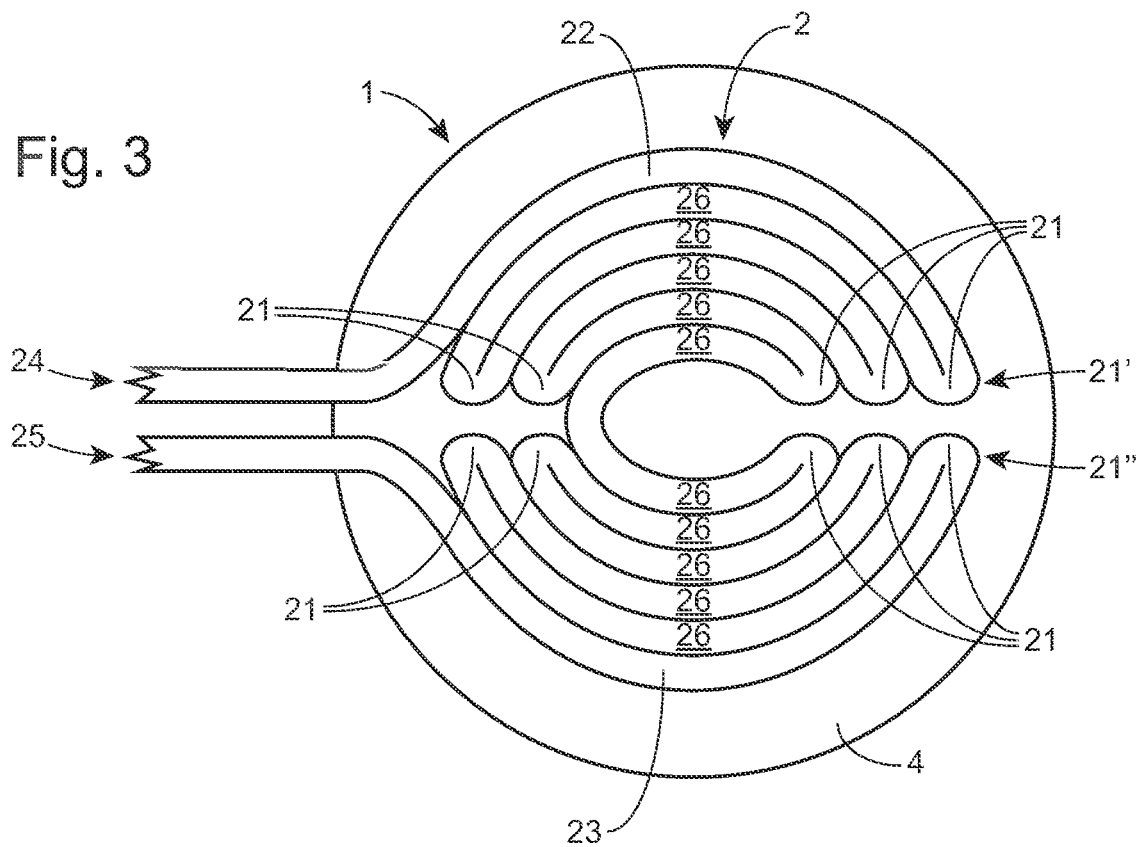
FIG. 3 is an illustration showing an implant for active agent delivery, according to embodiments of the present disclosure.

For a given length of the tubing on the surface of the scaffold, the length of tubing may define a first side external to the outer wall of the tubing within a plane parallel to the surface of the scaffold, and a second side external to the outer wall of the tubing opposite the first side. For the silicone tubing having a central switchback and a spiral pattern of a first and second lengths of the tubing, as described above, the distance between the first and second lengths, as well as the rate at which the first and second lengths of the tubing move away from the location of the central switchback may define the distance between a portion of the first length of tubing and a portion of the second length of tubing on a first side of the portion of the first length of tubing and the distance between the portion of the first length of tubing and a portion of the second length of tubing on a second side of the portion of the first length of tubing, opposite the first side. For example, in FIGS. 2A-B, the distance between the first 22 and second 23 lengths of the silicone tubing 2 and the rate at which the first and second lengths of the tubing move away from the location of the central switchback 21 are such that a portion of the first length of tubing and a portion of the second length of tubing on the first side of the portion of the first length of tubing are in contact with each other substantially along the spiral pattern, and the portion of the first length of tubing and a portion of the second length of tubing on the second side of the portion of the first length of tubing, opposite the first side, are in contact with each other substantially along the spiral pattern. By adjusting the distance between the first and second lengths of the tubing and the rate at which the first and second lengths of the tubing move away from the location of the central switchback, the total length of the silicone tubing 2 affixed to the scaffold 4 in a spiral pattern may be altered, to control the size of the target area to be treated and the amount of drug held in the depot of the implant 1, and contribute to achieving the desired profile of drug release. The distribution of the silicone tubing on the scaffold may also be adjusted to improve flexibility of the implant and facilitate furling or folding of the implant during surgical operations, as described herein.

The present implant can be an imageable implant, which can be imaged by any suitable imaging method after implantation. Thus, the implant can contain material that can be imaged using any suitable method, e.g., mammography, ultrasonography, magnetic resonance imaging (MRI), etc. The imageable material may be contained in any suitable component of the implant, e.g., in the silicone tubing, the scaffold, and/or the fill port, described further below. The imageable material may be any suitable material for use in imaging. In some embodiments, the imageable material includes metals, including non-magnetic metals, ceramic, or a radiopaque material. Radiopaque materials may include stainless steel, platinum, gold, iridium, tantalum, tungsten, silver, rhodium, nickel, bismuth or other radiopaque metals, mixtures of radiopaque metals, oxides of radiopaque metals, barium salts, iodine salts, iodinated materials, and combinations thereof. In some cases, the imageable material is a contrast agent, e.g., gadolinium, iron, platinum, manganese, and compounds thereof.

With reference to FIGS. 3, 4, 5 and 6 which illustrate alternative embodiments of the present implant, the silicone tubing 2 includes a plurality of switchbacks 21, a first switchback 21' proximal to a first end 24 of the tubing defining a first length of the tubing 22 between the first end and the first switchback, a second switch back 21" distal to the first switchback and proximal to a second end 25 of the tubing defining a second length of the tubing 23 between the second end and the second switchback, and pairs of consecutive switchbacks, including the first and second switchbacks, defining a number of internal lengths of the tubing 26, where the first, second and internal lengths of the tubing lie along each other so as to form, e.g., a cascading rows of arced (FIGS. 3 and 5) or parallel (FIGS. 4 and 6) lengths of the tubing. The distance between the outer walls of adjacent first, second and internal lengths of the tubing may vary, depending on the desired drug elution profile and handling properties of the implant, as discussed above. In some cases, the outer walls of adjacent first, second and internal lengths of tubing contact each other substantially along the lengths of the tubing. In some cases, there may be gaps between the outer walls of adjacent first, second and internal lengths of the tubing.

Figure 4:
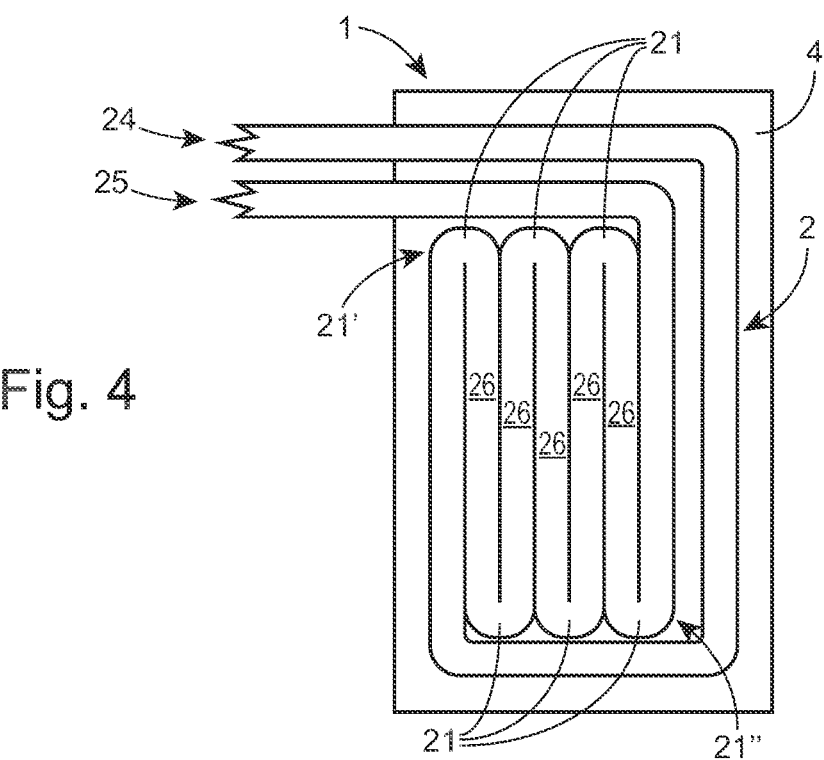
FIG. 4 is an illustration showing an implant for active agent delivery, according to embodiments of the present disclosure.
Figure 5:
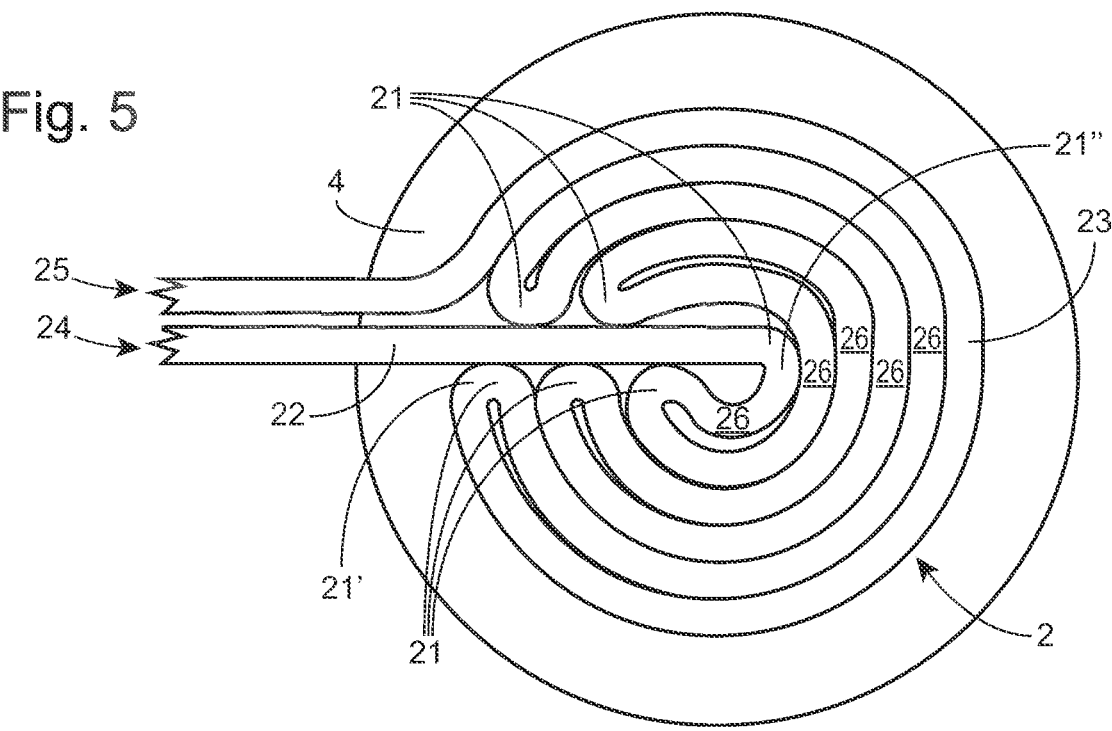
FIG. 5 is an illustration showing an implant for active agent delivery, according to embodiments of the present disclosure.
Figure 6:
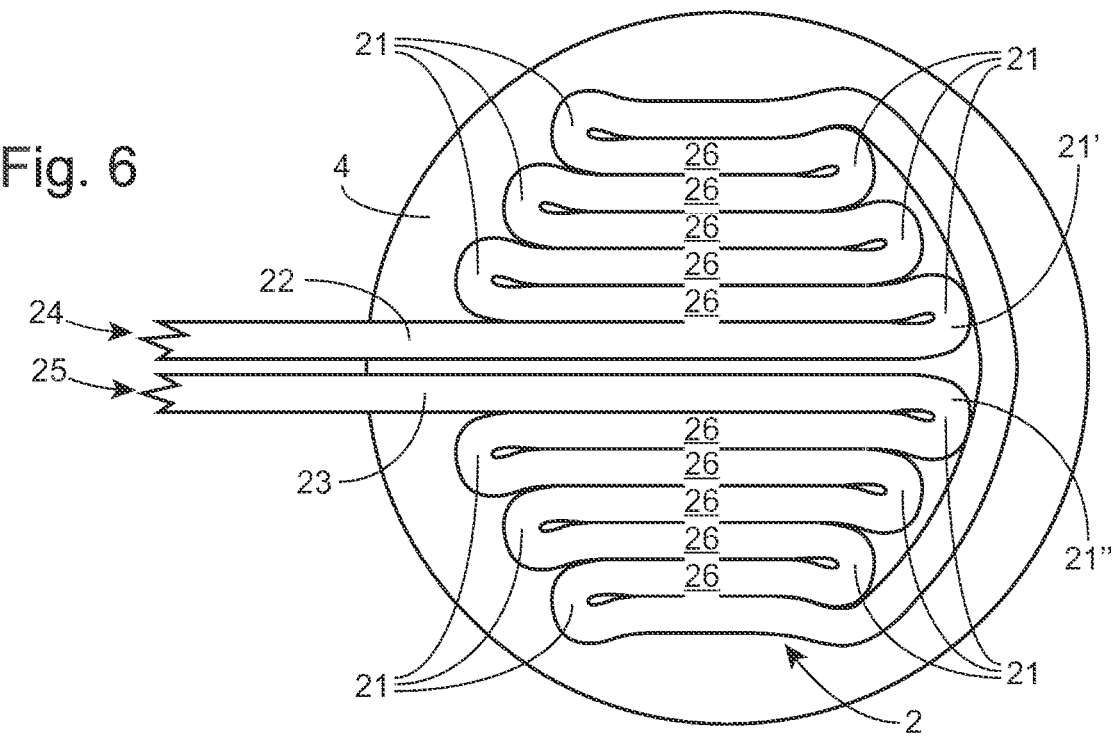
FIG. 6 is an illustration showing an implant for active agent delivery, according to embodiments of the present disclosure.

The surface onto which the silicone tubing is affixed defines a shape, which may be any suitable shape for attaching the silicone tubing, and may be adjusted based on the target tissue to be treated by the active agent and/or the physical dimensions of the implantation site. The shape of the scaffold in some cases is substantially circular (FIGS. 1A, 2A, 3, 5, 6), or is rectangular (FIG. 4).

Figure 8:
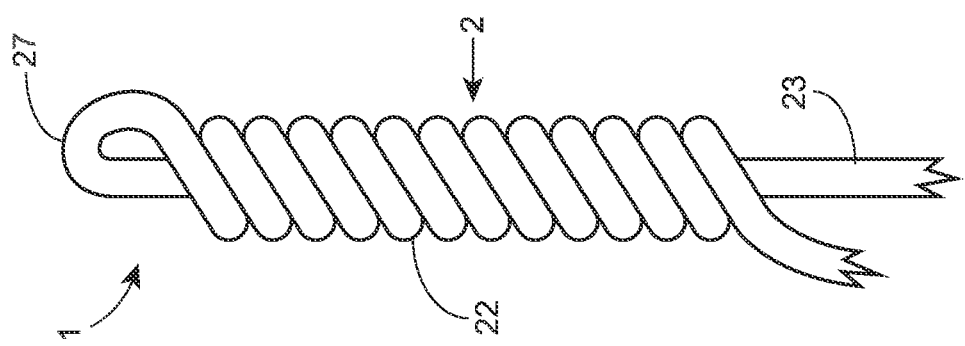
FIG. 8 is an illustration showing an implant for active agent delivery, according to embodiments of the present disclosure.
Figure 7:
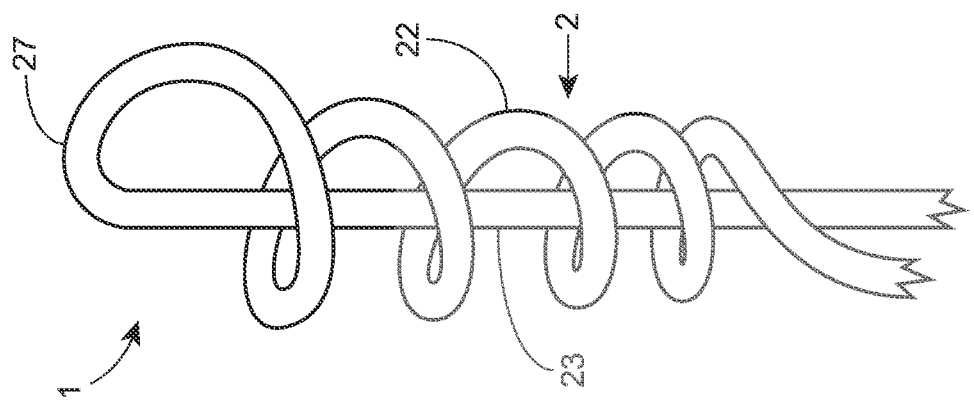
FIG. 7 is an illustration showing an implant for active agent delivery, according to embodiments of the present disclosure.

FIGS. 7 and 8 illustrate another embodiment of the present implant for drug delivery. The implant may include a silicone tubing 2, which contains a switchback in the form of a terminal loop 27 that defines a first length of the tubing 22 and a second length of the tubing 23. The second length of tubing may be substantially straight and define a central axis around which the first length of tubing forms a helical structure by winding around and along the central axis. The pitch, or distance between the outer wall of adjacent portions of the first length of the tubing at consecutive complete turns of the helix, may be adjusted as desired, and may be such that there is a gap between the portions (FIG. 7) or such that the outer walls of adjacent portions of the first length of the tubing at consecutive complete turns of the helix may be in contact with each other (FIG. 8). Thus, the pitch of the helix may be adjusted to control the amount of drug contained in the implant 1, and contribute to achieving the desired profile of drug release.

Figure 9:
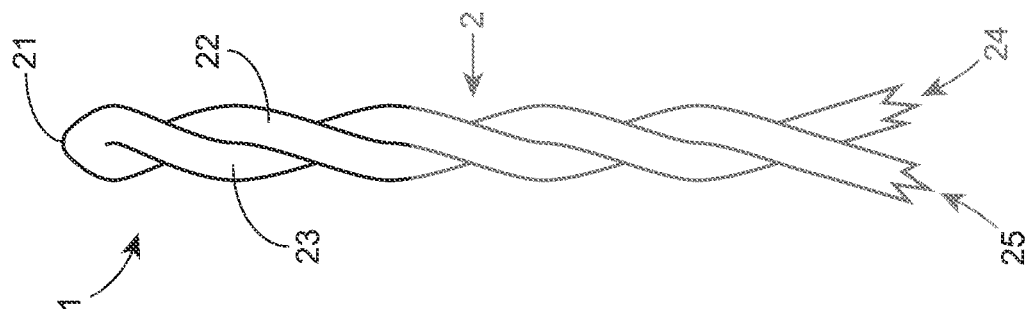
FIG. 9 is an illustration showing an implant for active agent delivery, according to embodiments of the present disclosure.

FIG. 9 shows an embodiment of the present implant for drug delivery 1 where the silicone tubing 2 includes a single switch back 21 located at the distal end. The switch back defines a first length of the tubing 22 and a second length of the tubing 23, where the first and second lengths of the tubing are intertwined with each other in double-helix form. The pitch of the helices and the total length of the tubing from the end of the first and second lengths to the switchback can be adjusted to fit the target tissue dimensions and to control the amount of drug held in the depot of the implant 1, to achieve the desired profile of drug release.

Figure 10A:
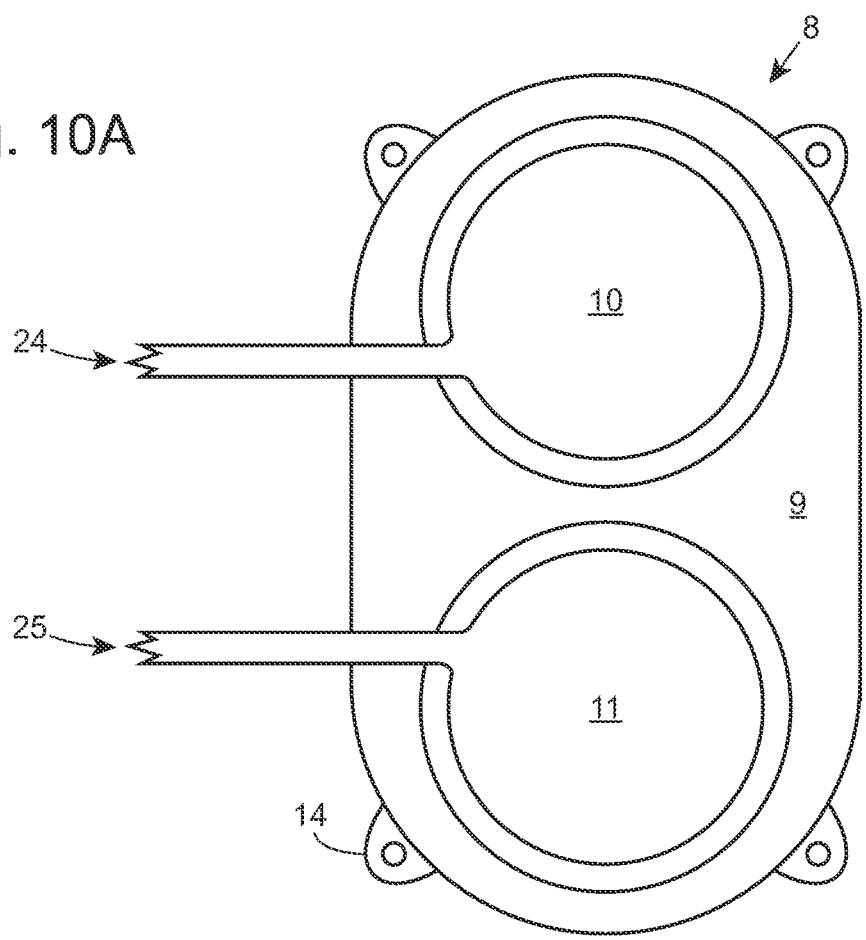
FIGS. 10A-B are illustrations showing a fill port for use in an implant for active agent delivery, according to embodiments of the present disclosure.
Figure 10B:
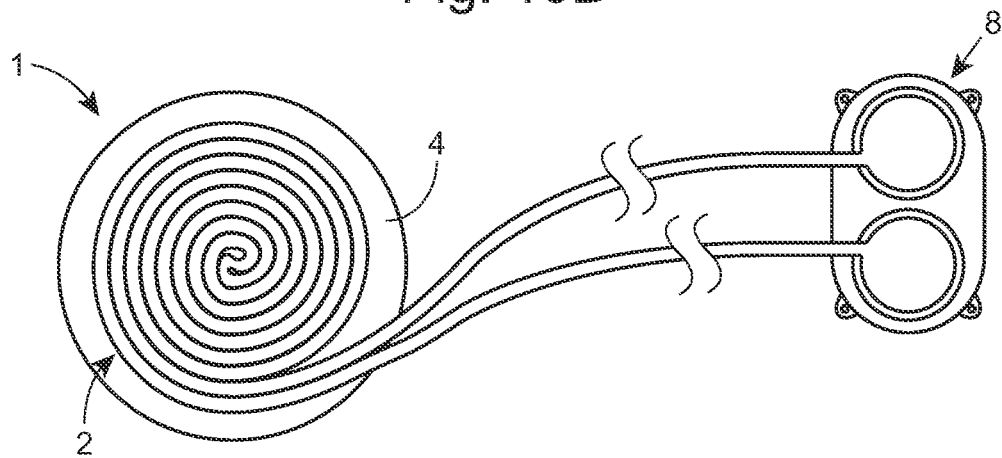

With reference to FIGS. 10A-B, there is shown the design for a remote fill port 8, which may be connected to the silicone tubing 2 to form a refillable, closed system. The remote fill port contains a solid detectable backing 9, which allows for, e.g., percutaneous locating of the port with a magnet finder if the backing is magnetic. There are two separate chambers in the port 10, 11, each feeding into a first end 24 and second end 25 of the silicone tubing, e.g., Silastic® silicone tubing, respectively. The port also contains suture tabs 14 at its base to allow for suturing to the soft tissue upon implantation, thus helping to resist turning or movement of the port.

FIGS. 11A-C illustrates a manner in which the silicone tubing 2 of the present implant may be filled with a displacing solution 204 by displacement of an initial content 202, e.g., for loading the tubing with a drug. The initial content may be a gas, e.g., air, or an initial solution, e.g., an organic solvent, and the displacing solution may be a drug solution. The silicone tubing is connected to a remote fill port, as described in FIGS. 10A-B, and the displacing solution is introduced into the tubing (FIG. 11A) through a first end of the tubing 24 by introducing the solution into a first remote fill port chamber connected to the first end of the tubing. The solution is moved through the tubing by any suitable method, including gravity flow, positive back pressure applied proximally to the first end of the tubing 24, and/or negative vacuum pressure applied proximally to the second end of the tubing 25. As the solution migrates into the silicone tubing of the implant (FIG. 11B), the initial content of the silicone tubing is displaced, pushed through the second end of the tubing and removed via a second remote fill port chamber. Eventually, the initial content of the tubing is displaced completely (FIG. 11C), without introducing any air pockets or other inhomogeneities through the tubing.

In certain cases, e.g., where the liquid flow through the silicone tubing is non-turbulent, the first and second ends are connected within the implant such that an amount of liquid introduced into the implant from the first end under sustained pressure will exit the implant from the second end when a volume of liquid in the implant approximately equal to the internal volume of the silicone tubing between the first and second ends is displaced by the applied pressure.

Figure 12:
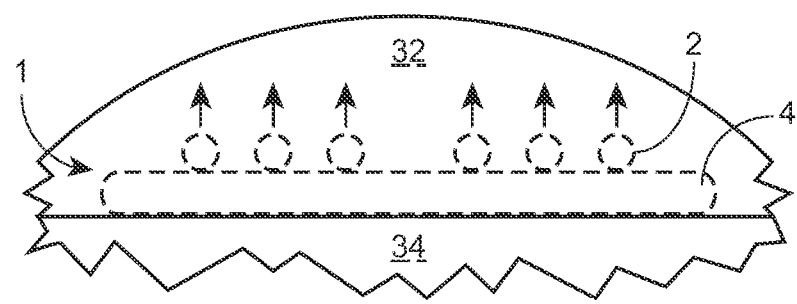
FIG. 12 is a schematic diagram showing an implant for active agent delivery implanted in a target tissue in situ, according to embodiments of the present disclosure.

As illustrated in FIG. 12, the implant 1, having a silicone tubing 2 affixed to a scaffold 4, when loaded with a drug, as described in FIGS. 11A-C, can provide localized, unidirectional delivery of the drug in a tissue in which the implant is placed. The implant is positioned such that the drug in the implant diffuses preferentially to a target tissue 32, while the scaffold prevents diffusion of the drug to a non-target tissue 34.

Figure 13A:
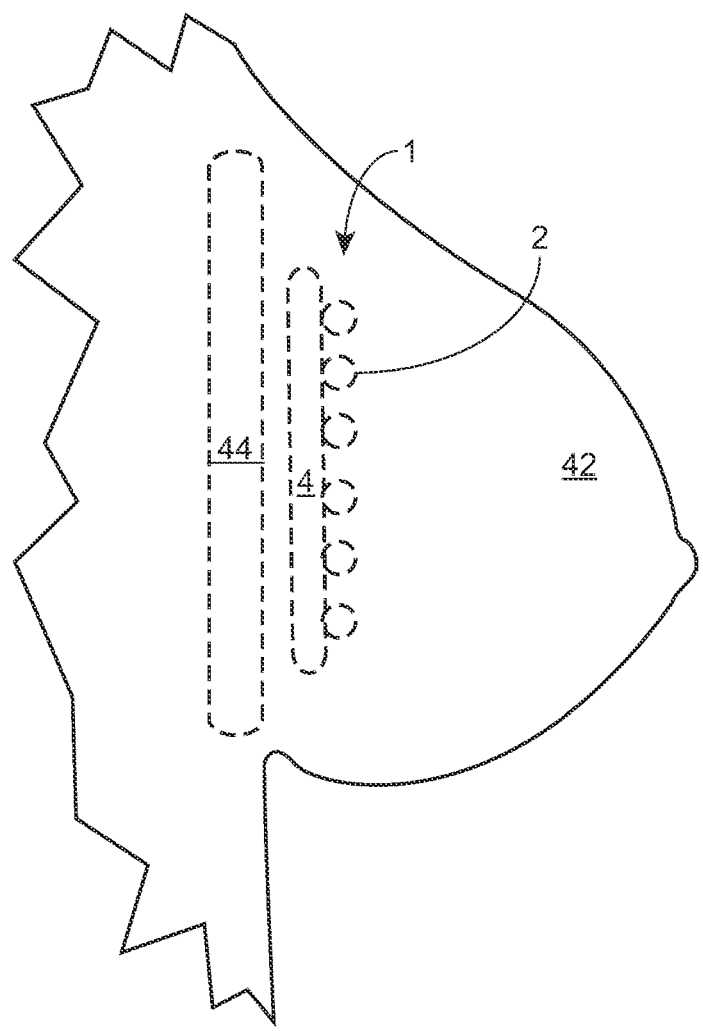
FIGS. 13A-B are illustrations showing an implant for active agent delivery implanted in a breast tissue, according to embodiments of the present disclosure.

With reference to FIG. 13A, there is shown an implant 1, having a scaffold 4, e.g., a breast implant, implanted in the breast 42. The implant is placed superficial to the pectoralis muscle 44. The silicone tubing 2, e.g., Silastic® Tubing, Functioning as the Drug Eluting Delivery system, is seen on the anterior surface of the scaffold 4, in direct contact with the overlying breast tissue. A drug, e.g., an antiestrogen drug, elutes from a drug-containing solution in the tubing into the breast tissue 42, but the breast implant hinders diffusion of the drug to the pectoralis muscle 44 and prevents systemic circulation of the drug.

Figure 13B:
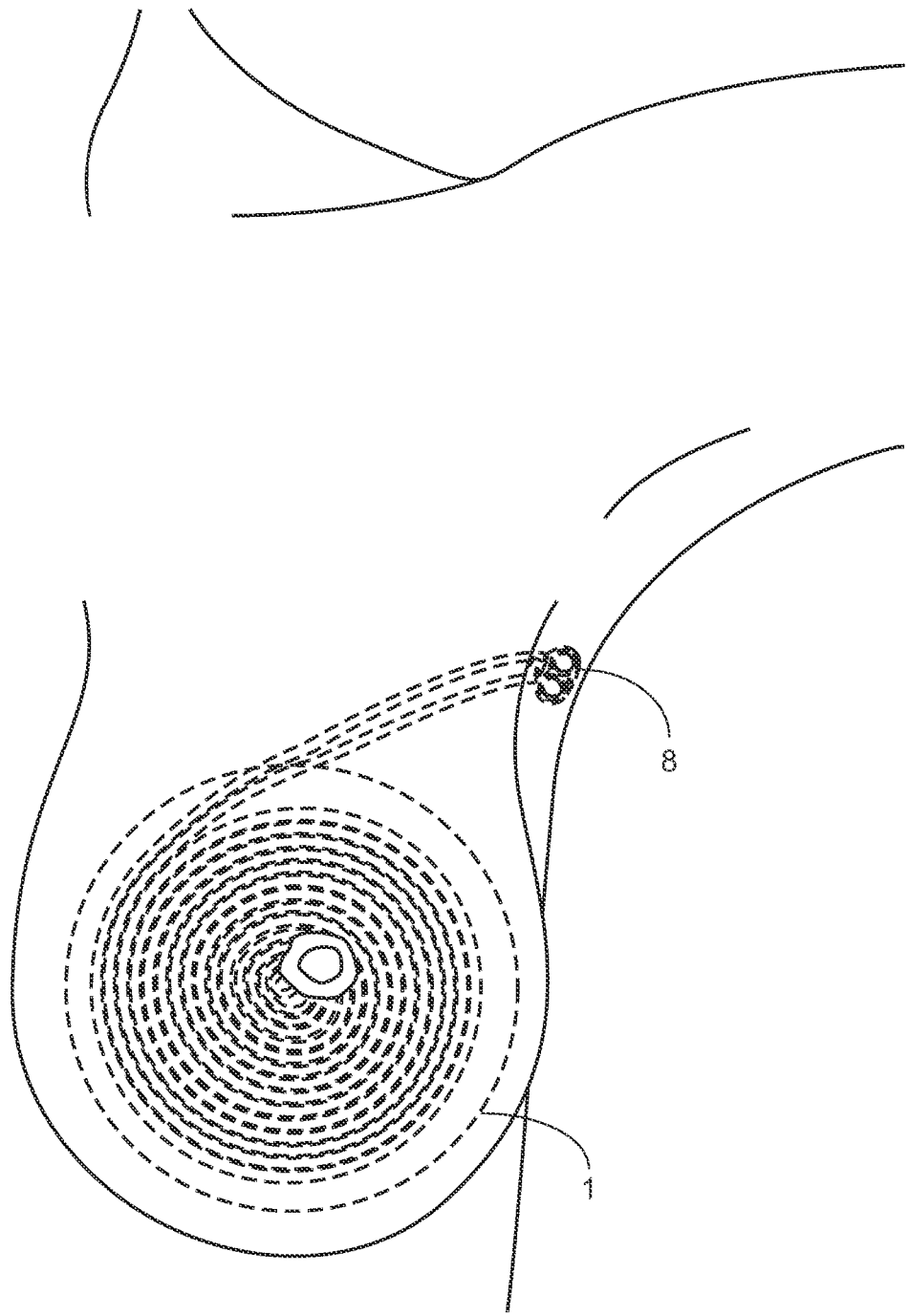

With reference to FIG. 13B, there is shown an implant 1 with a silicone tubing 2, e.g., Silastic® silicone tubing, affixed thereto, in anterior birds-eye view. The continuation of the tubing in each direction is directed to the remote fill port 8. The remote fill port may be implanted subcutaneously where it provides ready access to the contents of the silicone tubing in the implant for introducing and/or removing solutions. The remote fill can be implanted at any convenient location, such as in the axilla (as shown in FIG. 13B) or at the breast fold.

The present implant has sufficient flexibility so as to allow a medical practitioner, e.g., a surgeon, to furl or roll the implant into a more compact structure and facilitate placement of the implant during surgery. FIGS. 14A-D illustrate various ways in which the present implant may be furled for implantation. Starting from the initial planar configuration (FIG. 14A), in one case, two opposite ends of the scaffold 4 is rolled over on the side of the silicone tubing 2 to form a configuration suitable for delivery to a site of implantation (FIG. 14B). In addition to furling the ends, the center of the scaffold can be folded to further reduce the width of the cross-sectional profile of the implant to form a configuration suitable for delivery (FIG. 14C). In addition, the entire scaffold is rolled over from one end to another on the side of the silicone tubing to form a configuration suitable for delivery (FIG. 14D). Once the implant is placed in the tissue of interest, the implant is unfurled into its functional configuration, which can be similar to the initial planar configuration (FIG. 14A). The implant may be secured in place by any suitable means, such as one or more suture tabs affixed to the implant.

Figure 15:
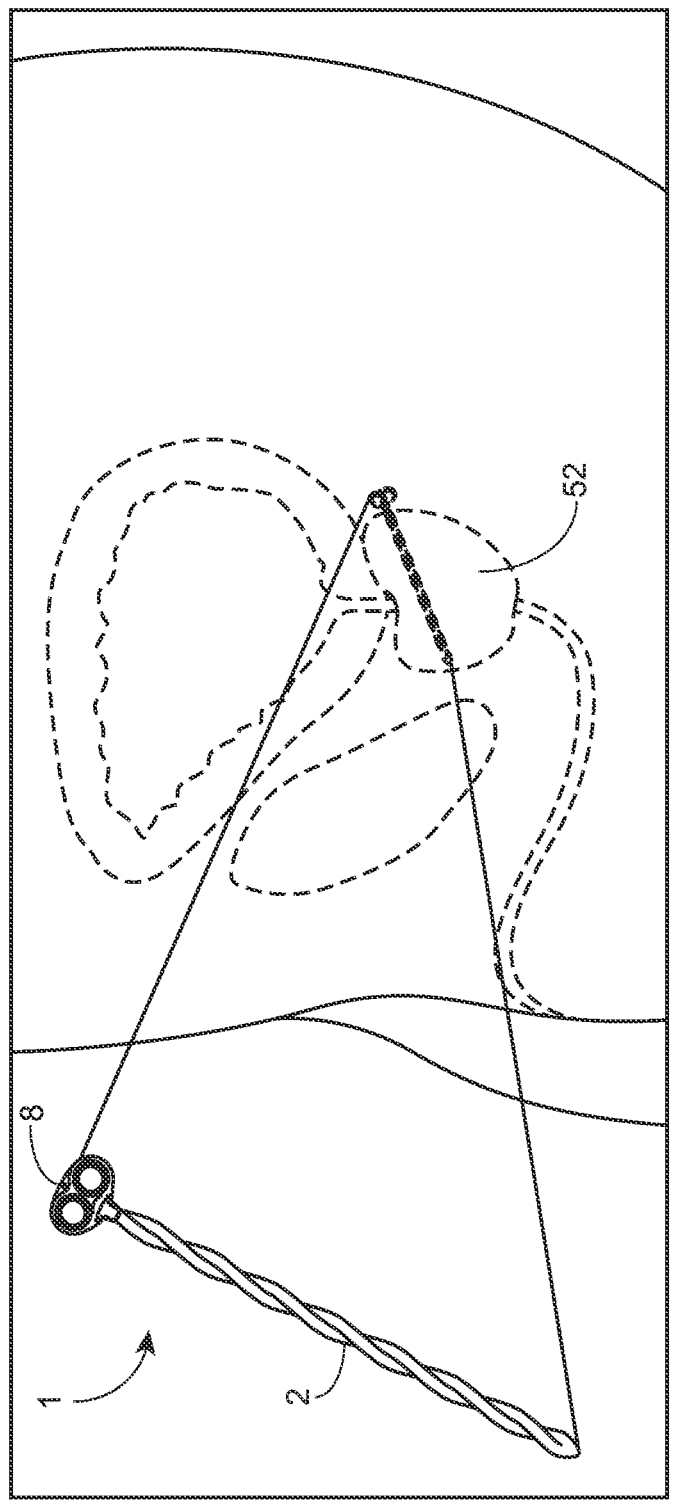
FIG. 15 is an illustration showing an implant for active agent delivery implanted in a prostate tissue, according to embodiments of the present disclosure.

FIG. 15 illustrates the placement of an embodiment of the present implant 1 in the prostate gland 52, in sagittal view. The silicone tubing 2 has an intertwined, double-helical form, as described in FIG. 9, and is sized to fit the prostate gland. A dual fill port 8 is attached to the ends of the silicone tubing and implanted under the skin to allow filling and removing of drugs as desired.

Silicone Tubing

The silicone tubing can be any biocompatible tubing that is permeable to a hydrophobic active agent of interest and allows for diffusion of the active agent through the wall of the tubing. The silicone tubing can be a biomedical grade, platinum-cured, elastomeric silicone tubing. Suitable silicone tubing includes SILASTIC silicone tubing available from Dow Corning Co. In some instances, the silicone tubing is SILASTIC-Rx50, having a shore value of around 50. Other exemplary silicone tubing is described in e.g., U.S. Pat. Nos. 3,279,996 and 4,012,497, which are incorporated by reference herein.

Without wishing to be held to theory, the Silastic® polymer may allow for the diffusion of various steroids under Fick's law of diffusion. Rate of steroid diffusion from the tube is primarily limited by solubility of the solute in the polymer matrix, rather than by the fluid boundary layer and will be geared by the solubility and amount of the active agent, e.g., a chemopreventive agent.

The silicone tubing can have any physical and material properties (e.g., inner diameter, wall thickness, flexibility, tensile strength, etc.) suitable for use in the present implant. The physical and material properties can in some cases be substantially uniform along the length of the tubing that is attached to the scaffold and/or is in direct contact with the target tissue so as to provide controlled delivery of the active agent.

The silicone tubing can have any dimensions suitable for delivering the active agent to a target tissue over the desired duration. The inner diameter of the silicone tubing may be 0.1 mm or more, e.g., 0.3 mm or more, 0.5 mm or more, including 0.6 mm or more, and may be 5.0 mm or less, e.g., 3.0 mm or less, 1.0 mm or less, including 0.9 mm or less. In some cases, the inner diameter of the silicone tubing is in the range of 0.1 to 5.0 mm, e.g., 0.1 to 3.0 mm, 0.3 to 1.0 mm, including 0.5 to 0.9 mm. The outer diameter of the silicone tubing may be 0.5 mm or more, e.g., 0.8 mm or more, 1.0 mm or more, including 1.2 mm or more, and may be 10 mm or less, e.g., 5.0 mm or less, 3.0 mm or less, including 2.0 mm or less. In some cases, the inner diameter of the silicone tubing is in the range of 0.5 to 10 mm, e.g., 0.8 to 5.0 mm, 1.0 to 3.0 mm, including 1.2 to 2.0 mm. The wall thickness of the silicone tubing may be 0.1 mm or more, e.g., 0.2 mm or more, 0.3 mm or more, including 0.4 mm or more, and may be 3.0 mm or less, e.g., 1.0 mm or less, 0.8 mm or less, including 0.6 mm or less. In some cases, the wall thickness of the silicone tubing is in the range of 0.1 to 3.0 mm, e.g., 0.1 to 1.0 mm, 0.2 to 0.8 mm, including 0.3 to 0.6 mm.

The length of the silicone tubing may vary depending on the desired amount of tubing (volume of the wall and/or the internal volume), the size of the implant, target tissue and/or implantation site, the desired profile of drug release from the implant, etc.

The silicone tubing is shaped in the present implant to serve as a depot for the active agent, a source of sustained release of the active agent, and to allow simple and efficient exchange of contents of the tubing. The silicone tubing can contain at least one switchback between the first and second ends of the tubing and the length of the tubing can outline a circuitous path such that a longer total length of the tubing can be contained in a space whose dimensions are smaller than the total length of the tubing than if the tubing were straight or not circuitous. In some cases, the tubing forms a single switchback and the two lengths of the tubing defined relative to the switchback are intertwined with each other into a double helical form. In some cases, the tubing is attached to a scaffold and outlines a circuitous path on the surface of the scaffold, as described in further detail herein.

Scaffold

The scaffold can be any biocompatible solid but flexible scaffold that is substantially impermeable to a hydrophobic active agent of interest and prevents diffusion of the active agent from one side of the scaffold to the other. The scaffold may be made of a material, e.g., a polymeric material, that is substantially impermeable to the hydrophobic active agent, and/or may have structural features (thickness, shape, etc.) that effectively prevent the hydrophobic active agent from diffusing from one side of the scaffold to the other. The scaffold can be a membrane, a film or a flexible sheet. In some cases, the scaffold may be a breast implant.

The scaffold can be non-degradable when implanted in a physiological environment. Thus, the scaffold may be sufficiently resistant to degradation by chemical, physical and/or enzymatic means when implanted at the target tissue, to retain its function as a scaffold and a barrier for diffusion of the active agent for the duration of use of the implant.

In some embodiments, the scaffold is made of a biocompatible polymeric material. Some relevant factors to be considered in choosing a polymeric material for the scaffold include: compatibility of the polymer with the biological environment of the implant, compatibility of the active agent with the polymer, ease of manufacture, a half-life in the physiological environment, etc. Depending on the relative importance of these characteristics, the compositions can be varied. Several such polymers and their methods of preparation are well-known in the art. See, for example, U.S. Pat. Nos. 4,304,765; 4,668,506; 4,959,217; 4,144,317, and 5,824,074, Encyclopedia of Polymer Science and Technology, Vol. 3, published by Interscience Publishers, Inc., New York, latest edition, and Handbook of Common Polymers by Scott, J. R. and Roff, W. J., published by CRC Press, Cleveland, Ohio, latest edition; which are incorporated herein by reference.

The polymers of interest may be homopolymers, copolymers, straight, branched-chain, or cross-linked derivatives. Suitable polymers include: polycarbamates or polyureas, cross-linked poly(vinyl acetate) and the like, ethylene-vinyl ester copolymers having an ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer, or mixtures thereof.

Additional examples include polymers such as: poly (methylmethacrylate), poly(butylnethacrylate), plasticized poly(vinylchloride), plasticized poly(amides), plasticized nylon, plasticized soft nylon, plasticized poly(ethylene terephthalate), natural rubber, silicone, poly(isoprene), poly (isobutylene), poly(butadiene), poly(ethylene), poly(tetrafluoroethylene), poly(vinylidene chloride), poly (acrylonitrile, cross-linked poly(vinylpyrrolidone), chlorinated poly(ethylene), poly(trifluorochloroethylene), poly(ethylene chlorotrifluoroethylene), poly(tetrafluoroethylene), poly(ethylene tetrafluoroethylene), poly(4,4'-isopropylidene diphenylene carbonate), polyurethane, poly(perfluoroalkoxy), poly(vinylidenefluoride), vinylidene chloride-acrylonitrile copolymer, and vinyl chloride-diethyl fumarate copolymer.

Some further examples of polymers include: poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinylolefins), poly(styrene), poly(halo-olefins), poly(vinyls) such as polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, polyvinyl acetate, ethylene vinylchloride copolymer, polyvinyl esters, polyvinylbutyrate, polyvinylformal, poly(acrylate), poly(methacrylate), poly(oxides), poly(esters), poly(amides), and poly(carbonates), or mixtures thereof.

The shape and dimensions of the scaffold may vary depending on the size of the target tissue and/or implantation site, the amount of tubing needed to achieve a desired profile of drug release from the implant, etc. In some embodiments, the scaffold is substantially planar. The scaffold may have any suitable thickness, and may have an average thickness that is 0.01 mm or more, e.g., 0.1 mm or more, 0.5 mm or more, 1 mm or more, 5 mm or more, 10 mm or more, including 20 mm or more, and may have an average thickness that is 40 mm or less, e.g., 30 mm or less, 20 mm or less, 10 mm or less, 5 mm or less, 1 mm or less, including 0.5 mm or less. In some embodiments, the scaffold has a thickness in the range of 0.01 to 30 mm, e.g., 0.1 to 20 mm, 0.1 to 10 mm, 0.5 to 10 mm, including 1 to 5 mm. The scaffold may be circular, oval, rectangular, square, etc. In some cases, the scaffold is substantially circular, having an average diameter of 0.1 cm or more, e.g., 1 cm or more, 2 cm or more, 5 cm or more, 8 cm or more, 10 cm or more, including 30 cm or more, and has an average diameter of 100 cm or less, e.g., 50 cm or less, 20 cm or less, 10 cm or less, including 5 cm or less. In some embodiments, a substantially circular scaffold has an average diameter in the range of 0.1 cm to 100 cm, e.g., 1 cm to 50 cm, including 1 cm to 20 cm.

The scaffold can be flexible enough such that the implant can be folded and/or rolled into a configuration suitable for delivery into the site of implantation through, e.g., a surgically made incision.

In embodiments of the present disclosure where the silicone tubing is affixed to a first surface that is opposite to a second surface of a scaffold, the silicone tubing can outline a circuitous path along the first surface. The circuitous path may be any suitable pattern, including a spiral, cascading lengths of tubing, etc.

The distance between portions of the tubing that lie next to each other in the circuitous pattern may vary. In some cases, the smallest distance between the outer walls of adjacent lengths of the tubing at a position along the circuitous path is, 0 fold or more, e.g., 0.1 fold or more, 0.2 fold or more, 0.3 fold or more, 0.5 fold or more, 0.75 fold or more, including 1.0 fold or more of the outer diameter of the tubing, and is 2.0 fold or less, e.g., 1.5 fold or less, 1.0 fold or less, 0.8 fold or less, 0.6 fold or less, 0.5 fold or less, 0.4 fold or less, including 0.3 fold or less of the outer diameter of the tubing. In some instances, the smallest distance between the outer walls of adjacent lengths of the tubing at a position along the circuitous path is in the range of 0 to 2.0 fold, e.g., 0 to 1.0 fold, 0 to 0.8 fold 0.1 to 0.6 fold, including 0.1 to 0.4 of the outer diameter of the tubing.

In some embodiments, by outlining a circuitous path, the silicone tubing covers a large fraction of the area of the first surface of the scaffold. In some cases, the silicone tubing covers 10% or more, e.g., 20% or more, 30% or more, 40% or more, 50% or more, 60% or more, 70% or more, including 80% or more, and covers 100% or less, e.g., 90% or less, 80% or less, 70% or less, 60% or less, including 50% or less of the first surface of the scaffold. In some cases, the silicone tubing covers 10% to 100%, e.g., 20% to 90%, 30% to 80%, including 40% to 70% of the area of the first surface of the scaffold.

The silicone tubing may be attached to the surface of the scaffold using any convenient method. In some embodiments, the silicone tubing may be attached to the surface of the scaffold with a biocompatible adhesive disposed between the surface and the tubing, or by using a fixation device such as a suture to stitch or sew the tubing onto the scaffold, etc.

The implant can include any suitable element for securing the implant to tissue at the site of implantation. In some cases, the implant includes one or more suture tabs. Any suitable suture tab may be used. In some embodiments, the scaffold includes one or more suture tabs that may be used to secure the implant at the site of implantation. In some cases, one or more suture tabs may be affixed to the silicone tubing fir use in securing the implant at the site of implantation.

Active Agents

The active agents that find use in the present implant for delivery are hydrophobic/lipophilic active agents. The hydrophobicity or lipophilicity of the hydrophobic compound, as defined by the distribution coefficient (log D) between water and octanol, may be 4 or higher, e.g., 4.5 or higher, 5 or higher, and may be 10 or less, e.g., 9.5 or less, including 9 or less. Thus, the hydrophobicity of the hydrophobic compound, as defined by log D between water and octanol, may be in the range of 4 to 10, or 4.5 to 9.

The active agent may be any suitable active agent for local delivery to a site of implantation by the present implant. In some instances, the active agent is an anti-cancer drug or a cancer chemopreventive drug, for, e.g., breast cancer, prostate cancer, etc.

In some embodiments, the hydrophobic active agent is a steroid. In some embodiments, a steroid active agent is an estrogen, including estradiol, or other agonists of the estradiol receptor. The steroid active agent may include 17 beta estradiol, 17 alpha estradiol and their hydroxylated metabolites with or without subsequent glucuronidation, sulfation, esterification or O-methylation; an estradiol precursor; an active estradiol metabolite such as estrone and estriol; an active analog such as mycoestrogens and phytoestrogens including coumestans, prenylated flavonoid, isoflavones (e.g. genistein, daidzein, biochanin A, formononetin and coumestrol).

In some embodiments, a steroid active agent is a modulator capable of positively influencing the activity of the estradiol receptor(s) or of enhancing the binding and/or the activity of estradiol towards its receptor such as a selective estrogen receptor modulator (SERM) including tamoxifen and a derivative thereof including 4-hydroxytamoxifen, clomifene, raloxifene, toremifene, bazedoxifene, lasofoxifene, ormeloxifenem, tibolone and idoxifene; a selective estrogen receptor down-regulator (SERD) including fulvestrant, ethamoxytriphetol and nafoxidine; and a high dose estradiol such as diethylstilbestrol and ethinyloestradiol; and testosterone. The log D for fulvestrant is around 8.47, tamoxifen is around 6.122 and raloxifene is around 5.406.

In some embodiments, a steroid active agent is a progestogen, such as progesterone or progesterone analogues. Other suitable progestogens may include, for example, allyloestrenol, dydrogesterone, lynestrenol, norgestrel, norethyndrel, norethisterone, norethisterone acetate, gestodene, levonorgestrel, medroxyprogesterone, and megestrol acetate.

In some embodiments, a steroid active agent is a modulator or inhibitor of the progesterone receptor. Suitable steroid active agent may include mifepristone (RU-486 or analogs thereof such as 11β-(4-dimethylaminophenyl)-17β-hydroxy-17α-(e-methyl-1-butynyl)-4,9-estradien-3-one and 11β-(4-acetophenyl)-17β-hydroxy-17α-(3-methyl-1-butynyl)-4,9-estradien-3-one.

In some embodiments, a steroid active agent is a testosterone, or precursors or derivatives thereof, such as 17 β-alkanoyl esters of testosterone, including $C_{1-15}$ saturated or unsaturated straight or branched chain alkanoyl esters, such as testosterone-17-acetate and testosterone-17-propionate, methyltestosterone, androstenedione, adrenosterone, dehydroepiandrosterone, oxymetholone, fluoxymesterone, methandrostenolone, testolactone, pregnenolone, 17α-methylnortestosterone, norethandrolone, dihydrotestosterone, danazol, oxymetholone, androsterone, nandrolone, stanozolol, ethylestrenol, oxandrolone, bolasterone and mesterolone, testosterone propionate, testosterone cypionate, testosterone phenylacetate, and testosterone enanthate, testosterone acetate, testosterone buciclate, testosterone heptanoate, testosterone decanoate, testosterone caprate, testosterone isocaprate, isomers and derivatives thereof, and a combination thereof.

In some embodiments, a steroid active agent is a corticosteroid. Examples of corticosteroids include fluocinolone, triamcinolone, cortisone, prednisolone, flurometholone, dexamethasone, medrysone, loteprednol, fluazacort, hydrocortisone, prednisone, betamethasone, prednisone, methylprednisolone, riamcinolone hexacatonide, paramethasone acetate, diflorasone, fluocinonide, derivatives thereof, and mixtures thereof.

In some embodiments, the lipid active agent is cholesterol, or derivatives thereof. Cholesterol derivatives may include 7β-hydroxycholesterol 7-ketocholesterol, 7-ketocholesteryl acetate, 25-hydroxycholesterol, 24,25-epoxycholesterol, diacetylenic cholesterol, cholest-4-ene-3,6-dione, cholest-4-en-3-one, cholesteryl behenate, cholesteryl benzoate, cholesteryl butyrate, cholesteryl caprate, cholesteryl caproate, cholesteryl caprylate, cholesteryl-3,5-dinitrobenzoate, cholesteryl formate, cholesteryl-β-D-glucoside, cholesteryl hemisuccinate, cholesteryl heptylate, cholesteryl heptadecanoate, cholesteryl hydrogen phthalate, cholesteryl isobutyrate, cholesteryl isovalerate, cholesteryl laurate, cholesteryl linoleate, cholesteryl methyl succinates, cholesteryl myristate, cholesteryl nervonate, cholesteryl-p-nitrobenzoate, cholesteryl oleate, cholesteryl oleyl carbonate, cholesteryl palmitate, cholesteryl palmitelaidate, cholesteryl palmitoleate, cholesteryl phosphoryl choline, cholesteryl polyethylene glycols, cholesteryl propionate, cholesteryl N-propyl carbonate, cholesteryl 1-pyreecarbonate, cholesteryl (pyren-1-yl) hexanoate, cholesteryl stearate, cholesteryl-P-tosylate, cholesteryl valerate, thiocholesterol, and cholesteryl sulfate.

Cholesterol derivatives may further include lanosterol, 14-nor-lanosterol, 14-nor,24,25-dihydrolanosterol, Δ7-cholestenol, 4α-methyl-Δ7-cholestenol, 4α-methyl-Δ8-cholestenol, dehydrocholesterol, cholestenone, cholestanone, cholestanol, coprosterol (coprostanol), coprostanone, Ia-hydroxycholesterol, 7α-hydroxy-4-cholesten-3 one, 5β-cholestan-3α,7α,12α,26-tetrol, 7α,12α-dihydroxy-4-cholesten-3-one, 5β-cholestan-3α,7α,12α-triol, 5β-cholestan-3α,7α-diol, 5β-cholestan-3α,7α,26-triol, 5-cholestene-3β,7β-diol, 5-cholestene-3β,20α-diol, 5-cholestene-3β,22(R)-diol, 5-cholestene-3β,22(S)-diol, 5-cholestene-3β,25-diol, 5α-choles-7-en-3β-ol, 5α-choles-3β-ol-7one, 5α-cholestan-3β-ol, 5β-cholestan-3α-ol, α1-sitosterol, β-sitosterol, γ-sitosterol, stigmasterol, stigmastanol, fucosterol, campesterol, ergostanol, α-ergostenol, β-ergostenol, γ-ergostenol, dinosterol, ergosterol, cholestane, cholestene, coprostane, ergostane, lanostane, and campestane.

Cholesterol derivatives may further include cholesterol acetate, cholesterol arachidonate, cholesterol behenate, cholesterol butyrate, cholesterol docosanoate, cholesterol dodecanoate, cholesterol eicosapentanoate, cholesterol elaidate, cholesterol erucate, cholesterol heptadecanoate, cholesterol heptanoate, cholesterol hexanoate, cholesterol linoleate, cholesterol α-linolenate, cholesterol γ-linolenate, cholesterol nonanoate, cholesterol octanoate, cholesterol oleate, cholesterol palmitate, cholesterol palmitoleate, cholesterol pentanoate, cholesterol propanoate, cholesterol tetracosanoate, cholesterol tetracosenoate, cholesterol methyl ether, cholesterol ethyl ether, cholesterol n-propyl ether, cholesterol 2-propyl ether, cholesterol 1-n-butyl ether, cholesterol 2-n-butyl ether, cholesterol isobutyl ether, and cholesterol tert-butyl ether.

In some embodiments, the hydrophobic active agent is an inhibitor of mediators of cellular signaling pathways, such as an inhibitor of poly adenosine diphosphate (ADP) ribose polymerase (PARP), mammalian target of rapamycin (m-TOR), Raf kinase and epidermal growth factor receptor (EGFR). In some embodiments, the hydrophobic active agent is a modifier of DNA methylation, such as a histone deacetylase inhibitor or a demethylation agent. In some embodiments, the hydrophobic active agent is an immunomodifier, such as an inhibitor of cytotoxic T-lymphocyte-associated protein 4 (CTL-4), programmed cell death protein 1 (PD-1), and anaplastic lymphoma kinase (ALK).

The hydrophobic active agent may be formulated in any suitable manner for loading the silicone tubing of the present implant, before or after implantation of the implant in a target tissue of a subject. The hydrophobic active agent may be solubilized in any suitable solvent, e.g., an organic solvent. The organic solvent may include ethanol, methanol, benzyl alcohol, benzyl benzoate, dimethylsulfoxide (DMSO), dimethylformamide (DMF), castor oil, etc., and combinations thereof. Other organic solvents include glycofurol, propylene glycol, polyethylene glycol 400, Lutrol® and dihydrolipoic acid.

In some embodiments, the hydrophobic active agent is present in the silicone tubing of the present implant. The hydrophobic active agent may be present within the wall of the silicone tubing, on the surface of the inner wall of the silicone tubing, and/or present in the internal volume of the silicone tubing in liquid form, e.g., dissolved in a solution in the tubing. In some embodiments, the active agent is present in the tubing at a concentration, per cm of tubing, of 0.0001 mg or more, e.g., 0.001 mg or more, 0.005 mg or more, 0.01 mg or more, 0.05 mg or more, 0.1 mg or more, including 1 mg or more, and is present in the tubing at a concentration, per cm of tubing, of 10 mg or less, e.g., 5 mg or less, 1 mg or less, 0.1 mg or less, 0.5 mg or less, including 0.1 mg or less. In some embodiments, the active agent is present in the tubing at a concentration, per cm of tubing, in the range of 0.0001 to 10 mg, e.g., 0.001 to 1 mg, including 0.01 to 0.1 mg.

Fill Port

In some embodiments, the present implant includes a fill port configured to provide access to the internal volume of the silicone tubing, before and after implantation. The fill port can include one or more chambers/lumens, where each lumen can be connected to an end of the silicone tubing that extends out from the portion of the implant that resides or is intended to reside at the target tissue. Thus, each of the two ends of the silicone tubing of the present implant may be connected to a chamber of a fill port. Any suitable solution may be introduced into the silicone tubing of the implant by applying the solution to one fill port, allowing the solution to displace the contents of the tubing, and removing the displaced contents through the second fill port. In some embodiments, the fill port is a dual lumen fill port having two chambers, each chamber being in fluid communication at the fill port with one end of the silicone tubing. The fill port may be implanted subcutaneously at any convenient site on the subject.

The fill port may have other features that can facilitate the use of the implant. In some embodiments, the fill port includes a detectable backing. In some cases, the fill port includes a magnetic backing to facilitate locating of the fill port using a magnet finder. In some cases, the detectable backing is an imageable backing, e.g., a backing that is compatible with an imaging system, such as mammography, ultrasonography, magnetic resonance imaging (MRI), etc. In some instances, the fill port includes suture tabs at its base for suturing the fill port to the tissue after implantation.

Methods

Method of Delivering a Hydrophobic Active Agent

Also provided herein is a method of locally delivering a hydrophobic active agent to a target tissue in a subject, by placing an implant of the present disclosure in a target tissue. The implant is positioned in the target tissue such that the active agent is released from the silicone tubing and delivered to the target tissue in a sustained manner over a time period. Where the implant includes a scaffold to which the silicone tubing is attached, the implant can be oriented such that the scaffold serves to prevent or reduce diffusion of the active agent into non-target tissue, such as muscle and other highly-vascularized tissue, to reduce off-target side effects and/or systemic side effects. Thus the implant of the present disclosure can achieve localized delivery of the active agent to target tissue.

In some embodiments, implanting includes folding or furling the implant into a configuration suitable for delivery of the implant into the implantation site. Such a delivery configuration will depend on the material properties the silicone tubing, and if present, the scaffold, and on the shape of the silicone tubing and/or scaffold. Thus, in some cases, two opposite edges of a scaffold may be furled towards the middle, wrapping the silicone tubing inside the fold, to reduce the width of the implant. In some embodiments, the middle of the implant may further be folded to form a ridge to further reduce the width of the implant. In other instances, the scaffold may be rolled from one end to the other, wrapping the silicone tubing inside the fold, to reduce the width of the implant. Any other suitable method may be used to reduce the length of the longest dimension of the scaffold and facilitate insertion of the implant into the site of implantation.

Once the implant is placed at the implantation site in its delivery configuration, the scaffold may be unfurled into its functional configuration. The functional configuration is one that provides for the localized, unidirectional delivery of the active agent to the target tissue, as described herein. The implant in its functional configuration may also be secured at the implantation site using any suitable means, including suturing to the target tissue.

The implant may or may not be loaded with the active agent before the implanting procedure.

The target tissue may be any suitable target tissue for implanting the present implant for delivering a hydrophobic active agent. In some embodiments, the target tissue is breast tissue. In some cases, an implant with a scaffold may be surgically placed over the pectoralis muscle and under the breast tissue, with the surface of the scaffold to which the silicone tubing is attached facing the ventral (or anterior) direction, toward the breast tissue, and the opposite surface of the scaffold facing the dorsal (or posterior) direction, toward the pectoralis muscle. In some embodiments, the target tissue is prostate tissue. In some cases, the implant without a scaffold may be positioned in the prostate through a rectal incision. In some embodiments, the target tissue is uterine, brain, skin, ovarian, gastrointestinal, bladder, muscle, liver, kidney or pancreatic tissue.

A non-target tissue to which the active agent is not delivered or delivered at a reduced level compared to the target tissue by the present implant may include blood (e.g., whole blood, blood serum, etc.), and may also include other tissues depending on the target tissue. In some cases, where the target tissue is breast tissue, the non-target tissue may include the pectoral muscle.

The subject may be any suitable subject, e.g., human subject, who may be in need of treatment by administration of the hydrophobic active agent. In some cases, the subject is a subject diagnosed with a disease, e.g., a cancer, such as breast cancer or prostate cancer. In some cases, the subject is a subject at risk of developing a disease, e.g., cancer, such as breast cancer. In such cases, the active agent may be an anti-cancer drug that can reduce the tumor burden, slow the progression of the cancer, retard or prevent tumorigenesis and/or retard or prevent the recurrence of a tumor in the subject.

The present implant provides for release of an amount of the active agent into the surrounding environment, e.g., surrounding tissue, when loaded with the active agent. In some cases, the implant releases the active agent at an average rate of 1 ng per cm of tubing per day or more, e.g., 3 ng per cm of tubing per day or more, 5 ng per cm of tubing per day or more, 7 ng per cm of tubing per day or more including 10 ng per cm of tubing per day or more, and releases the active agent at an average rate of 50 ng per cm of tubing per day or less, 40 ng per cm of tubing per day or less, 30 ng per cm of tubing per day or less, 20 ng per cm of tubing per day or less, including 10 ng per cm of tubing per day or less. In some cases, the implant releases the active agent at an average rate of 1 to 50 ng per cm of tubing per day, e.g., 1 to 30 ng per cm of tubing per day, 2 to 20 ng per cm of tubing per day including 3 to 10 ng per cm of tubing per day.

In some embodiments, the implant achieves an average level of the active agent in the target tissue of 50 nM or more, e.g., 75 nM or more, 100 nM or more, 125 nM or more, including 150 nM or more, and achieves an average level of the active agent in the target tissue of 1,000 nM or less, e.g., 800 nM or less, 600 nM or less, 400 nM or less, including 300 nM or less. In some embodiments, the implant achieves an average level of the active agent in the target tissue in the range of 50 to 1,000 nM, e.g., 75 to 600 nM, 100 to 400 nM, including 100 to 300 nM.

The implant can deliver the active agent in an amount effective to functionally alter cellular function and/or biochemical signaling pathways in the target tissue. The cellular function and biochemical signaling pathways may include expression level (protein or mRNA) of a receptor targeted directly or indirectly by the active agent, and/or proliferation of tumor cells.

In some embodiments, the implant delivers a therapeutically effective amount of the active agent to the target tissue.

The active agent delivered specifically to a target tissue using the present implant may be present in a non-target tissue at significantly lower level than in the target tissue. In some embodiments, the active agent delivered specifically to a target tissue is present in non-target tissue, such as in blood, at a lower percentage compared to the target tissue by 50% or more, e.g., 75% or more, 80% or more, 85% or more, 90% or more, 95% or more, 98% or more, 99% or more, up to about 100%, and is present at a lower percentage by 100% or less, 99% or less, 98% or less, 97% or less, 95% or less, 90% or less, 85% or less, including 80% or less. In some embodiments, the active agent delivered specifically to a target tissue is present in non-target tissue, such as in blood, at a lower percentage compared to the target tissue in the range of 50 to 100%, e.g., 75 to 100%, 85 to 100%, 90 to 100%, including 95 to 100%.

In some embodiments, the active agent delivered specifically to a target tissue may be present in non-target tissue, such as in blood, at an average level of 10 nM or less, e.g., 8 nM or less, 5 nM or less, including 4 nM or less. In some embodiments, the active agent delivered specifically to a target tissue may be substantially undetectable in the non-target tissue, such as in blood.

The implant of the present disclosure can provide sustained release of the active agent into the target tissue with a single loaded dose of the active agent. In some cases, the active agent is released for 5 days or more, e.g., 1 week or more, 5 weeks or more, 10 weeks or more, 20 weeks or more, 50 weeks or more, 2 years or more, 5 years or more, including 10 years or more, and is released for 60 years or less, e.g., 50 years or less, 40 years or less, 10 years or less, 1 year or less, including 26 weeks or less, into the target tissue with a single loaded dose of the active agent. In some embodiments, the active agent is released into the target tissue with a single loaded dose of the active agent for a time period in the range of 5 days to 60 years, e.g., 1 week to 50 years, 5 weeks to 40 years, 10 weeks to 10 years, including 20 weeks to 1 year.

Method of Loading and Reloading the Implant

The present implant including a silicone tubing depot for a hydrophobic active agent can be loaded and reloaded, before or after implantation. This allows for control of the dosage, type of drug or removal of an active agent from the implant in a simple manner. In some cases, the tubing may be connected at the ends to a fill port, as described above. The tubing can be filled by applying a solution to one end of the tubing, e.g., via a chamber on the fill port, letting the solution flow through the tubing towards the opposite end of the tubing. The solution may advance through the tubing by gravitational flow, or a pressure may be applied to the tubing. The pressure may be a positive pressure pushing the solution from the end to which the solution is initially applied, or may be a negative pressure applied to the opposite end of the tubing to draw the solution into the tubing.

Where the tubing is substantially uniform in inner diameter throughout the implant, a steady, gradual flow of the solution allows for the solution to fill the tubing without introducing air bubbles or local inhomogeneities.

Using such a method, the tubing may be filled with a solution containing an active agent. Removal of the solvent subsequent to filling, e.g., by evaporation, can result in the active agent being deposited on the inner surface of the wall of the tubing, thereby loading the tubing with the active agent. The solution may also be left in the tubing and the tubing may be sealed at both ends, thereby loading the tubing with the active agent. An active agent loaded in the tubing may be removed from the tubing by filling the tubing with a solution into which the active agent can diffuse out of the wall of the tubing. It is also possible to change the concentration of active agent in the tubing, switch the type of active agent present in the tubing, etc.

The implant, including the silicone tubing and/or fill port, and the active agent may be imaged when implanted, e.g., by mammography, ultrasonography, magnetic resonance imaging (MRI), etc. Thus, the imageable nature of the implant and the active agent may facilitate refilling and/or removal of solution from the implant.

In some embodiments, the tubing may be loaded with an active agent during the manufacture of the tubing, such as through room temperature vulcanization of the silicone elastomer.

Utility

The present implant for delivering a hydrophobic active agent and methods of use thereof find applications where it is desirable to provide sustained delivery of the active agent locally to a target tissue with reduced side effects, and reduced frequency dosage administration. For example, the present implant may find use in preventative intervention for breast cancer. Thus, in some embodiments, an implant of the present disclosure may be loaded with an anti-estrogen, such as fulvestrant, and surgically placed in breast tissue of patients predisposed to or at high risk of developing breast cancer. The exposure to systemic drug and resulting toxicity can be substantially reduced by localized delivery, increasing compliance. For female patients unwilling to give up their opportunity for conception or have their breasts removed at a stage in their life, the present implant could provide the necessary risk reduction until a future point where risk reduction surgery would be more acceptable. Furthermore, a refillable and reversible tubing as well as the imageable nature of the implant will allow for dose modification or complete removal and thus enable the plasticity required for adjustment to life events.

In certain embodiments, the present implant finds use in treating cancer by locally delivering a hydrophobic active agent to the cancerous tissue. The treatment outcome may include reducing the size of the tumor, slowing the progression of the cancer, and/or eliminating the tumor. In some cases, the cancer is a hormone responsive cancer, such as breast cancer and prostate cancer. In some cases, the cancer is uterine cancer, brain cancer, skin cancer, ovarian cancer, gastrointestinal cancer, bladder cancer, liver cancer, kidney cancer or pancreatic cancer.

Kits

Also provided herein is a kit that includes the present implant and that finds use in performing methods of the present disclosure. The kit may also include a packaging that includes a compartment, e.g., a sterile compartment, for holding the implant. The packaging may be any suitable packaging for holding the present implant. Examples of implant packaging and methods of packaging an implant are described in, e.g., U.S. Pat. Nos. 3,755,042, 4,482,053, 4,750,619; U.S. App. Pub. Nos. 20050268573, 20100133133, which are incorporated herein by reference.

In some cases, the implant in the packaging is pre-loaded with an active agent. In some embodiments, the kit includes one or more of various solutions that find use in loading, reloading, or unloading the silicone tubing of the present implant, as described above. The different components of the kit may be provided in separate containers, as appropriate.

The present kit may also include instructions for using the present implant and practicing the present methods. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

All publications and patent applications cited in this specification are herein incorporated by reference as if each individual publication or patent application were specifically and individually indicated to be incorporated by reference.

EXAMPLES

As can be appreciated from the disclosure provided above, the present disclosure has a wide variety of applications. Accordingly, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Efforts have been made to ensure accuracy with respect to numbers used (e.g. amounts, dimensions, etc.) but some experimental errors and deviations should be accounted for.

Example 1

Materials and Methods

General description of materials and methods used in the Examples are described below, unless indicated otherwise.

Preparation of Fulvestrant

Fulvestrant (25 mg) was dissolved in 1.5 mL ethanol under aseptic conditions. The resulting solution was 27.4 mM and used for all experiments described below.

Silastic® Tubing

The Silastic® tubing used was platinum-cured, translucent, Silastic® silicone tubing. This is an FDA approved product.

Drug Loading

Silastic® tubing (0.76 mm I.D., and 1.65 mm O.D.) was cut into 10 cm length tubes and fulvestrant solution was loaded using a 1 ml tuberculin syringe with a 20-gauge needle with a void of 1 cm. The tubes were left to dry for a predetermined time to desiccate, leaving a residue of fulvestrant inside the tube. These tubes were sealed with an adhesive and left to be cured for 48 hours resulting in an inseparable seal, or clipped with titanium 'Surgiclips™'. The seal was confirmed prior to further testing.

Drug Release in Saline

Fulvestrant loaded Silastic® tubing was incubated in saline and rocked at 37° C. Every 84 hours the saline was collected and replaced with fresh saline. The concentration of fulvestrant released in each sample of saline was determined by liquid chromatography-mass spectrometry (see below). Preliminary experiments were conducted using 0.076 mg fulvestrant per 1 cm tubing.

Drug Release in Culture Media

Each sealed (10 cm) tube was immersed into a 10 cm culture tube containing 5 mL culture media (Dulbecco's Modified Eagle's medium (DMEM)+10% fetal bovine serum (FBS)+penicillin and streptomycin) approximating interstitial tissue surrounding the breast tissue. These tubes were set on a rocker in an incubator at 37° C. for 1, 2, 5, 10, 15, 21 and 30 days. After each time point media was collected and stored at −80° C. for further analysis for western blotting, viability/proliferation assay by MTS (3-(4,5-dimethylthiazol-2-yl)-5-(3-carboxymethoxyphenyl)-2-(4-sulfophenyl)-2H-tetrazolium) and quantitation by liquid chromatography-tandem mass spectrometry (LC-MS/MS). Additional iteration was to perform repeated washes on the same sealed tube and collect the culture medium at days 1, 2, 5, 10, 15, 21, and 30.

Results with Collected Media

MCF-7 culture were propagated and seeded in 6 cm dishes at 300,000 cells per dish and allowed to adhere overnight as a monolayer. On day 0, medium in each dish was replaced with the collected drug medium (described above) that contained fulvestrant elutions of prespecified time periods (1, 2, 5, 10, 15, 21, 30 days, Appropriate reference samples included drug free medium, and direct administration of 100 nM fulvestrant (control)). The drug concentrations and biological effects of the drug eluted from specific tubes were evaluated by Mass spectroscopy, Western Blot analysis and antiproliferative methods after exposure for 3 days.

Western Blotting

Cell lysates (described above) were used to evaluate the down-regulation of the estrogen receptor, progesterone receptor and initial attempts for PS2.

MTS Assay

Separate cultures were set in a 96-well format (1000 cells/well) for a 3-day exposure to medium collected from the tubes incubated for either 1, 2, 5, 10, 15, 21, 30 days along with a set of untreated controls and culture treated with 100 nM fulvestrant. At the end of the exposure, medium was replaced by MTS dye diluted (200 µL per well) in culture medium and incubated for up to 2 hours at 37° C. Optical density (490 nm) at the end of the time points (1, 1.5 and 2 hours) was measure and plotted as a ratio of absorbance (day/untreated).

LC-MS/MS

A validated LC-MS/MS method was used for quantitation of fulvestrant. Sample was prepared by liquid-liquid extraction procedures with n-hexane-isopropanol (90:10, v/v). Extracts were concentrated (using a nitrogen stream at room temperature) and derivatized with 2 volumes of mobile phase buffer, and injected into a Sciex ultra performance liquid chromatorgraphy (UPLC) coupled with a Sciex API 5000™ triple quadrupole mass spectrometer. Data was acquired and analyzed by Analyst® MS software.

In Vivo Assays

Figure 21:
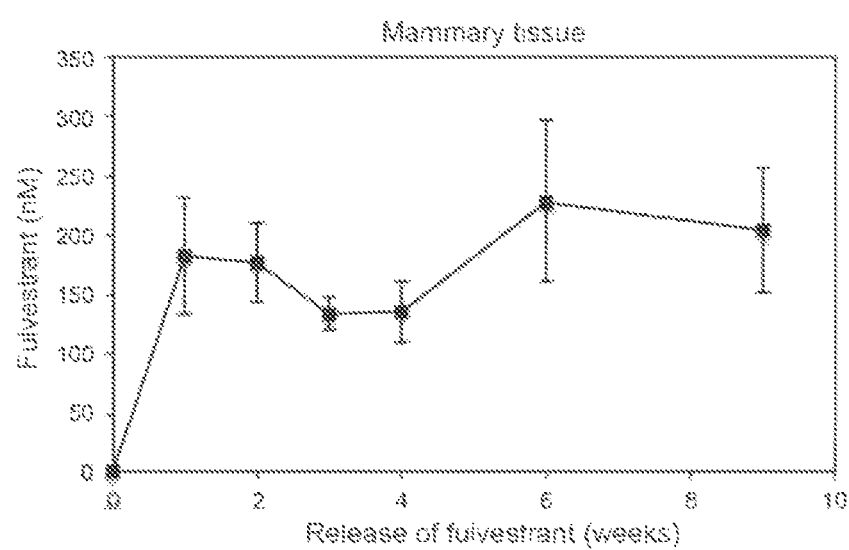
FIG. 21 is a graph showing amounts of fulvestrant measured in mammary tissue from mice implanted with a fulvestrant-loaded implant in mammary tissue, according to embodiments of the present disclosure.

Silastic® depot with dry fulvestrant was implanted subcutaneously and adjacent to the inguinal mammary fat pad of CD-1 female mice. Mice were monitored for body weight loss, activity, adequate grooming, and general behavior daily for the first week, followed by alternate days up to 10 months. Mice were euthanized and blood and organs were collected after 1, 2, 3, 4, 6 and 9 weeks (FIGS. 21 and 22). The level of fulvestrant in blood was determined to ensure estimated fulvestrant level was achieved. Organs were visually examined for overt pathology (e.g. color, size, and general condition) and exhibited none over the 9 week period.

Plasma and Tissue Collection and Processing

Blood from anaesthetized CD-1 female mice were collected in Vacutainer® tubes coated with $K_2$ ethylenediaminetetraacetic acid (EDTA) via cardiac puncture. Plasma was separated by centrifugation at 6,000×g for 10 minutes and stored at −80° C. Following blood collection, the mammary fat pads of mice exposed to fulvestrant administration via tubing were harvested and the amount of fulvestrant taken up by the tissue quantified. Harvested tissue was homogenized in saline on ice and then subjected to liquid-liquid phase extraction and evaluated for their levels of fulvestrant by LC-MS/MS as described above.

Example 2

Use of Silastic® Tubing as a Fulvestrant Depot

Figure 16:
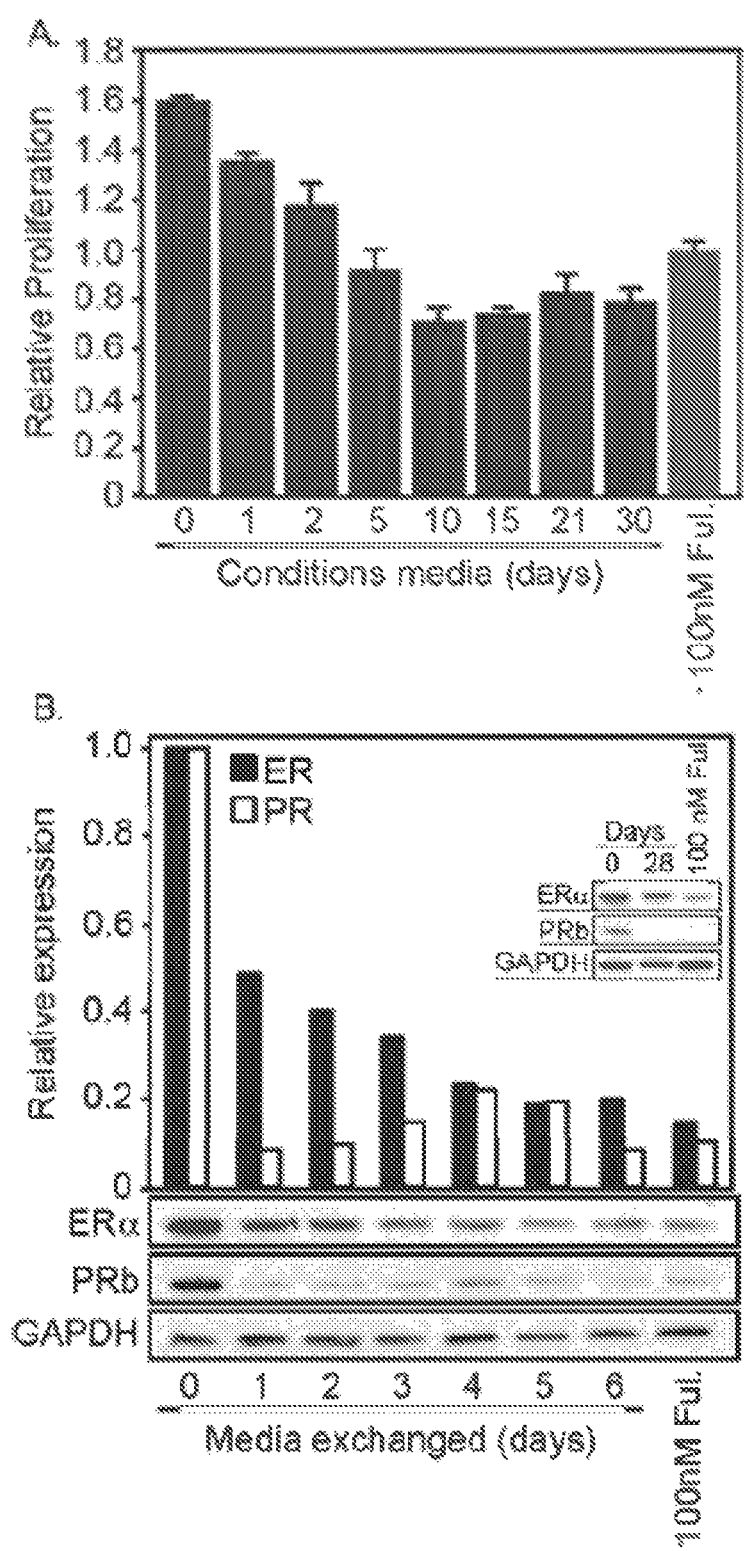
FIG. 16, panels A and B, is a collection of graphs showing the measured activity of fulvestrant eluted into media from a fulvestrant-loaded Silastic® tubing, according to embodiments of the present disclosure.
Figure 17:
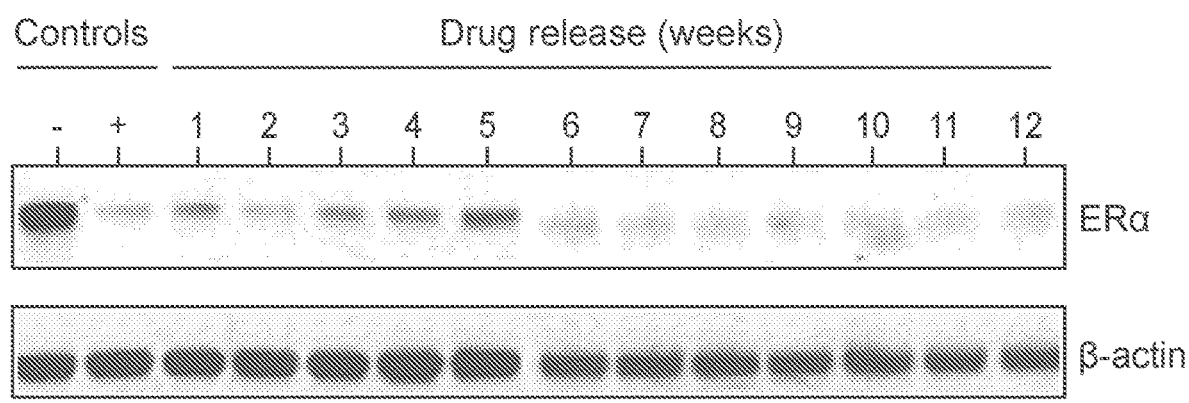
FIG. 17 is an image showing the activity of fulvestrant eluted into media from a fulvestrant-loaded Silastic® tubing, according to embodiments of the present disclosure.
Figure 18:
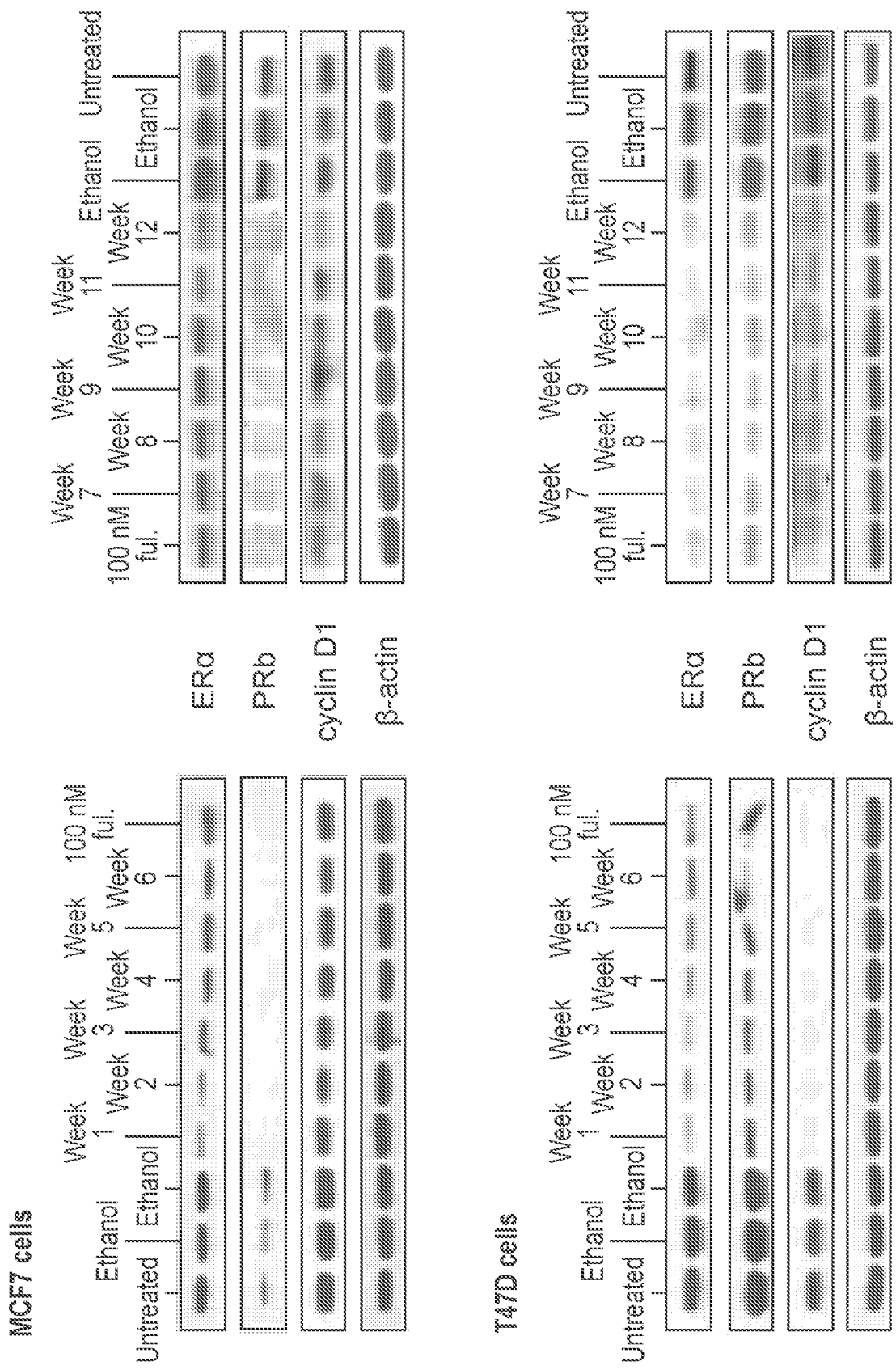
FIG. 18 is a collection of images showing the activity of fulvestrant eluted into media from a fulvestrant-loaded Silastic® tubing, according to embodiments of the present disclosure.

Our preliminary data shows that Silastic® tubing is capable of acting as a fulvestrant depot. Silastic® tubing (9 cm, medical grade Rx50 OD 1.65 mm, ID 0.76, FIG. 1C) was loaded with dry fulvestrant (0.076 mg/cm) and placed in tissue culture media for increasing times up to 30 days. Media containing tubing released drug at respective times was then added to cultured MCF7 ER-positive breast cancer cells and grown for 72 hours. Concentration curves of fulvestrant spanning clinically achievable concentrations of fulvestrant (10-50 nM) and up to a 10 µM were evaluated for antiproliferative effects at 72 hours showing all the concentrations were sufficient to block estrogen receptor signaling and proliferation. With an initial delay, as expected by the Silastic® tube kinetics, drug transfer for fulvestrant from the tubing was comparable to 100 nM of fulvestrant directly added to the culture media. Tube equilibration was sufficient within 2-5 days to achieve growth inhibition and estrogen receptor down regulation comparable to cells directly treated with fulvestrant (100 nM) (FIG. 16, panels A and B). Daily washout experiments further demonstrate that drug release from the Silastic® tubing for each 24-hour period is comparable and is sustained for at least 28 days. Weekly fulvestrant release was also consistent for more than 4 weeks in cell culture models, as measured by ER and PR down regulation (inset in FIG. 16, panel B), up to and beyond 12 weeks (FIGS. 17 and 18). Further data showed that this approach is amenable to drug transfer for raloxifene, 4-hydroxytamoxifen and estradiol (see Example 5).

FIG. 16, panels A-B: Silastic® tubing (9 cm) was loaded with 0.68 mg fulvestrant and incubated in 5 mL medium at 37° C. for the indicated time (Panel A) or harvested every 24 hours and replenished with fresh and replenished with fresh medium (Panel B). The medium was then used to culture MCF7 cells for 72 h, and the cells were assayed for proliferation by MTS assay (Panel A) and harvested for protein and western blotted for ER and PR expression (Panel B). Inset in Panel B demonstrates sufficient fulvestrant release to inhibit ER and PR expression for at least 28 days. As a positive control, MCF7 cells were treated directly with 100 nM fulvestrant (last bar in Panel A), a concentration sufficient to down regulate ER expression and arrest cell growth.

FIG. 17: Fulvestrant released from Silastic® implant was sufficient to inhibit target (e.g. estrogen receptor (ER)) in breast cancer cells (MCF7) up to 12 weeks. Controls included untreated MCF7 breast cancer cells (−) and MCF7 breast cancer cells treated with a clinically achievable dose (100 nM) of fulvestrant (+).

FIG. 18: Fulvestrant released from the Silastic® tubing sustains down-regulation of ER expression in MCF7 and T47D cells beyond 12 weeks. As negative controls, the cells were untreated or treated with media incubated with ethanol-loaded tubing. As a positive control, the cells were directly treated with 100 nM fulvestrant.

Figure 19:
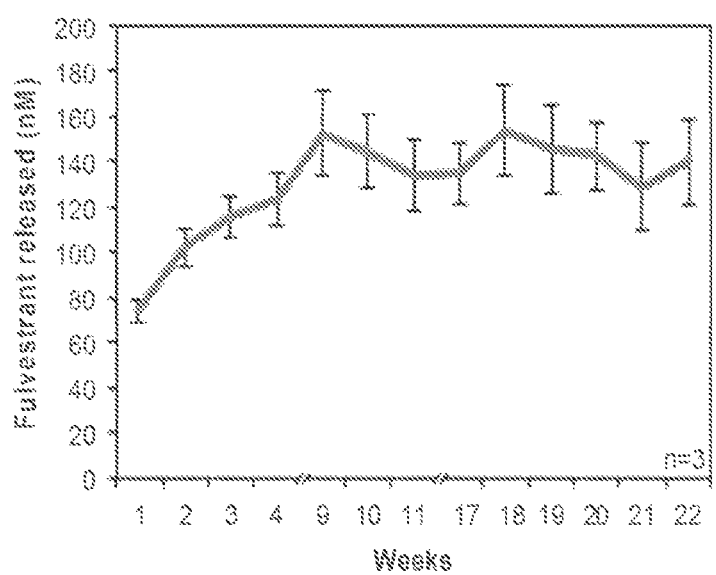
FIG. 19 is a graph showing measured amounts of fulvestrant eluted into media from a fulvestrant-loaded Silastic® tubing, according to embodiments of the present disclosure.

Release of fulvestrant from loaded Silastic® tubing into culture medium, as described above, was measured using LC-MS/MS and was sustained for up to 22 weeks (FIG. 19).

FIG. 19: Fulvestrant released from the Silastic® tubing in culture medium. Media was harvested semi-weekly (84 hrs).

Figure 20:
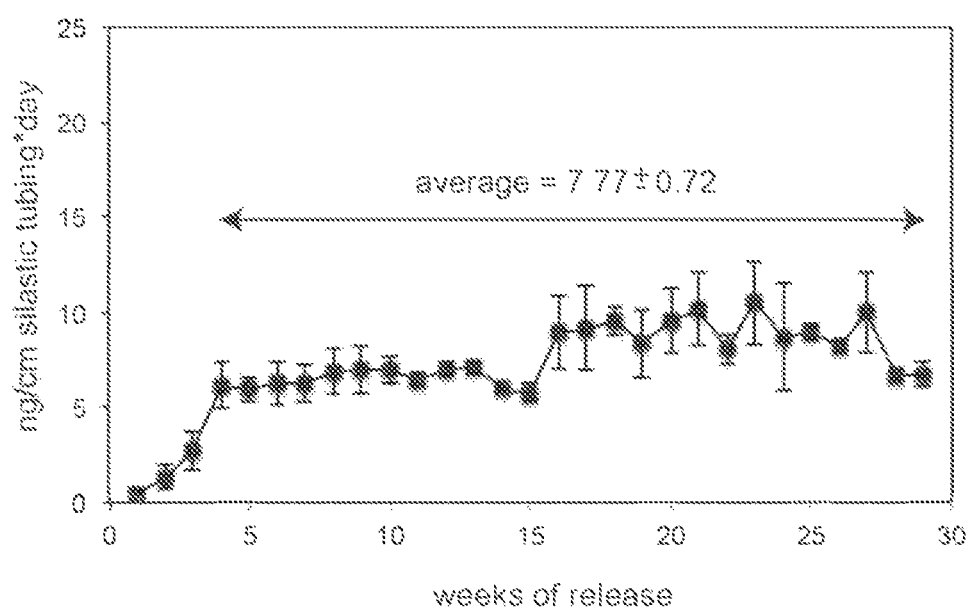
FIG. 20 is a graph showing measured amounts of fulvestrant eluted into saline from a fulvestrant-loaded Silastic® tubing, according to embodiments of the present disclosure.

Release of fulvestrant from loaded Silastic® tubing into a saline solution was measured using LC-MS/MS (FIG. 20). After 5 weeks, the rate of fulvestrant released remained steady with an average of 7.77 ng/cm tubing*day, exceeding 7 months. Based on this rate of release and the amount of fulvestrant in the device, the extrapolated duration of release exceeds 10 years.

FIG. 20: Four Silastic® devices were loaded with fulvestrant and immersed in saline and continuously rocked at 37 C. Every 84 hours, saline was collected and replaced with fresh saline. Fulvestrant was quantified in collected saline by liquid chromatography mass spectrometry.

Example 3

Localized and Sustained Release of Fulvestrant in Mammary Tissue

FIG. 21: A silastic device containing fulvestrant was implanted into female mice (CD-1) adjacent to their inguinal mammary tissue. The mice were implanted with 2 cm RX50 silastic tubing containing 0.076 mg/cm dry fulvestrant adjacent to the inguinal mammary fat pad. After the indicated number of weeks the mice were euthanized and tissue was harvested. The concentration of fulvestrant was measured in the blood and mammary tissue of 4 mice using liquid chromatography mass spectrometry.

In all but one mouse at week 4, fulvestrant was undetectable in blood (<4 nM; Table 1 in FIG. 22), whereas significant fulvestrant was detectable in the mammary tissue of all mice.

Example 4

Use of Silastic® Tubing as an Estradiol Depot

The effect of estradiol released from Silastic® tubing loaded with estradiol and placed in culture medium was monitored, using conditions similar to that described in Example 2. Sustained increased in progesterone receptor (PgR) mRNA expression was observed for up to 15 days (FIG. 23).

Figure 23:
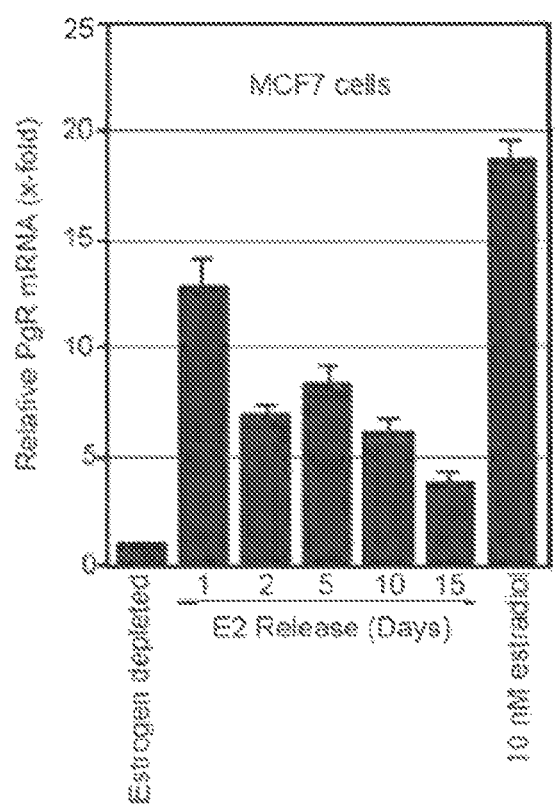
FIG. 23 is a graph showing measured activity of estradiol eluted into media from an estradiol-loaded Silastic® tubing, according to embodiments of the present disclosure.

FIG. 23: Drug (E2) was loaded into 3 independent silastic tubes, dried, and sealed before incubating them in tissue culture medium for the indicated number of days. The tubes were then removed and MCF7 cells were treated with the medium. For the E2 experiment, MCF7 cells were first depleted of E2 by growing for 48 hours in FBS stripped media. Then, after 24 hours of treatment with media containing released E2, cells were harvested and progesterone receptor mRNA was quantified by quantitative real-time (qRT)-polymerase chain reaction (PCR) using TaqMan® probes from Applied Biosystems. As controls, MCF7 cells untreated and treated directly with 10 nM E2 were run.

Example 5

Formulation of Fulvestrant Loaded Silastic® Tubing

Two key aspects of formulation are solubility and stability. Fulvestrant is a highly lipophilic compound that precludes its formulation in aqueous based excipients. For clinical use, fulvestrant has been developed as a long acting (~1 month) intramuscular formulation (Faslodex®, AstraZeneca Pharmaceuticals), by solubilizing up to 50 mg/mL in 10% ethanol, 10% benzyl alcohol, 15% benzyl benzoate, and to 100% with castor oil. Additional formulations have been developed that exhibit stability and comparable to or greater then solubility concentrations achieved with the Faslodex® formulation. These formulations use combinations of organic solvents, glycofurol, dihydrolipoic acid, and poloxamers. In addition to dry powder and Faslodex® fulvestrant formulations, three additional formulations are evaluated: (1) 50% glycofurol/50% propylene glycol (200 mg/mL), (2) 50% glycofurol/50% polyethylene glycol 400 (200 mg/mL), and (3) 20 mg Lutrol® in dihydrolipoic acid (350 mg/mL). Thus, in total, five fulvestrant formulations are compared as described below. For each formulation, PK parameters including Cmax, Tmax, Elimination Rate, Half-life and AUC (Area_under_Curve) over-time are estimated with descriptive statistics for comparison.

Example 6

Evaluation of Anti-Estrogen Implant in an In Vivo Goat Model

To evaluate the effectiveness of the Silastic® anti-estrogen implant in a large animal model mimicking the human female mammary system and anatomy, female alpine goats are used. Using the alpine goat model, the implant are tested for: 1) feasibility for surgical subglandular placement, 2) directional delivery of fulvestrant distal into mammary tissue, 3) the concentration and diffusion of fulvestrant through mammary tissue overtime, 4) the biodistribution of released fulvestrant in major organs and blood, 5) fibrotic capsule formation in proximity to the implant, and 6) resultant organ pathology and toxicity. These six outcomes are evaluated by surgically implanting a single device (10 cm in diameter containing 5 meters of silastic tubing loaded with 0.076 mg/cm tubing of fulvestrant) in the subglandular region of the udder in 3 female alpine goats. Every 7 days, blood and a mammary tissue biopsy are collected and evaluated for fulvestrant concentration. On day 28, the goats are sacrificed and organs are examined for overt pathology. Major organs, blood, and mammary tissue are collected and fulvestrant concentration is determined in each. Additionally, a blood chemistry panel and complete blood count are conducted at study initiation and conclusion to assess potential toxicity. Diffusion of fulvestrant through breast tissue is measured by sampling tissue at intermediate distances distally from the implant to the udder nipple during each biopsy. Implant and surrounding tissue are collected together at the conclusion of the study and are evaluated for fibrotic capsule formation by immunohistochemical analysis.

Example 7

Determining the Efficacy of Fulvestrant Released from Silastic® Tubing to Prevent Tumor Formation 2 cohorts of 15 4-6 weeks old female nude athymic Crl;NU(NCr)-Foxn1$^{nu}$ mice, totaling 30 mice, are implanted with 5×10⁶ breast cancer cells (1:1 v/v with Matrigel™) in the Inguinal mammary fat pad. Two days prior to tumor cell implantation, a 60-day release estrogen pellet is implanted subcutaneously in the flank of each mouse. Cohort 1 is implanted with 4 cm of Silastic® tubing loaded with vehicle. Cohort 2 is implanted with 4 cm of Silastic® tubing loaded with formulated fulvestrant. For both cohorts 1 and 2, Silastic® tubing is placed in the subcutaneous space proximal to the inguinal fat pad cell implantation 5 days prior to cell implantation. Tumor volumes, by caliper measurement, and weights are assessed three times weekly. Animals are monitored daily for toxicity and are euthanized if tumors exceed 1.5 cm in its largest diameter, total volume exceeds 2000 mm³, or when mice exhibit pain or distress.

Preliminary work has shown that fulvestrant released from Silastic® tubing is sufficient to abrogate ER signaling and reduce cell proliferation of MCF7 cells in vitro. To determine whether these pharmacodynamic effects extend to tumors in vivo, tumors are harvested immediately post euthanasia and divided into four parts for protein, RNA, immunohistochemical analysis, and fulvestrant extraction. Each technique are evaluated for expression of ER, ER response genes, and key proliferative genes/proteins including PgR, cyclin D1 and E, pS2, EBAG9, p21, p27, c-Myc, and Ki-67. As described above, concentrations of fulvestrant in plasma, organs and tumor tissue are determined by LC-MS/MS. The fulvestrant released from Silastic® tubing is dichotomized into two groups as low and high based on the median (or from the observed cutpoint of the data distribution). The expression of ER, ER response genes and key proliferative genes/proteins expression is compared between the dichotomized fulvestrant groups. T-test is used for the mean difference of each expression between groups.

While embodiments of the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method of treating prostate cancer in a subject, the method comprising:
providing a depot comprising a silicone implant having at least one silicone wall loaded with a hormone-modulating active agent, wherein said at least one silicone wall is permeable to said hormone-modulating active agent and the only means for the hormone-modulating active agent to exit the silicone implant is by diffusing through the at least one silicone wall,
the depot having a first, second and third orthogonal dimension, and wherein a length (h) of the silicone implant is longer than the longest dimension of the first, second and third orthogonal dimension,
implanting the depot into or adjacent a prostate with the at least one silicone wall abutting the prostate;
the depot delivering said hormone-modulating active agent to said prostate in said subject as said hormone-modulating active agent diffuses through the at least one silicone wall when implanted in said prostate in said subject.

2. The method of claim 1, wherein said silicone implant is elastomeric silicone tubing.

3. The method of claim 1, wherein said hormone-modulating active agent is selected from the group consisting of cholesterol, estradiol, progesterone, testosterone, corticosteroid, derivatives thereof, and synthetic analogs thereof.

4. The method of claim 1, wherein said hormone-modulating active agent is present in said depot at a concentration of about 0.0001 mg to about 10 mg per cm of depot.

5. The method of claim 1, wherein said delivery of said hormone-modulating active agent to said prostate is at an average level of about 50 nM to about 1000 nM of said hormone-modulating active agent in said prostate.

6. The method of claim 1, wherein a level of said hormone-modulating active agent in blood plasma is about 95% or less when compared to a level of said hormone-modulating active agent in said prostate.

7. The method of claim 1, wherein said hormone-modulating active agent is present in a non-target tissue from a substantially undetectable level to about 10 nM.

8. The method of claim 1, wherein said depot is configured to deliver said hormone-modulating active agent to said prostate for about 5 weeks to about 10 years.

9. The method of claim 1, wherein said hormone-modulating active agent is selected from the group consisting of an anti-estrogen, an anti-androgen, a selective estrogen receptor modulator (SERM), and a selective estrogen receptor down-regulator.

10. A method of modulating hormone levels in a target tissue in a subject, the method comprising:
implanting a depot comprising a polymeric implant such that a polymeric wall of the polymeric implant abuts said target tissue;
wherein said polymeric implant comprises, prior to implanting:
the polymeric wall extending between a first end of the polymeric implant and a second end of the polymeric implant;
an active agent distributed throughout said polymeric wall, wherein said polymeric wall is permeable to said active agent, wherein the only means for the active agent to exit the polymeric implant is by diffusing through the polymeric wall;
the depot having a first, second and third orthogonal dimension, and wherein a length (h) of the polymeric implant is longer than the longest dimension of the first, second and third orthogonal dimension; and
the polymeric implant directly delivering said active agent to said target tissue in said subject as said active agent is released through said polymeric wall when implanted in said target tissue.

11. The method of claim 10, wherein said active agent is a steroid.

12. The method of claim 10, wherein said active agent is an antiandrogen.

13. The method of claim 10, wherein said active agent is selected from the group consisting of an anti-estrogen, an anti-androgen, a selective estrogen receptor modulator (SERM), a selective estrogen receptor down-regulator, and an inhibitor of poly adenosine diphosphate (ADP) ribose polymerase (PARP).

14. The method of claim 10, wherein said polymeric implant is fabricated from non-biodegradable material.

15. The method of claim 10, wherein said target tissue comprises breast tissue or prostate tissue.

16. The method of claim 10, wherein said active agent is present in said polymeric implant at a concentration of about 0.0001 mg to about 10 mg per cm of polymeric implant.

17. The method of claim 10, wherein after said implanting, an average level of said active agent in said target tissue is in the range of about 50 nM to about 1000 nM.

18. The method of claim 10, wherein said active agent is present in a non-target tissue from a substantially undetectable level to about 10 nM.

19. The method of claim 10, wherein said polymeric implant delivers a sustained release of said active agent to said target tissue.

20. The method of claim 10, wherein said polymeric implant delivers said active agent to said target tissue for about 5 weeks to about 10 years.

21. The method of claim 10, wherein said polymeric wall comprises a polymer matrix and wherein said active agent is distributed throughout said polymer matrix.

22. A method of treating prostate cancer in a subject, the method comprising:

implanting a depot in a prostate in said subject, wherein said depot comprises, prior to said implanting:

a polymer matrix having a plurality of surface areas which face different directions and having substantially uniform physical and material properties;

a hormone-modulating active agent distributed within said polymer matrix, wherein said polymer matrix is permeable to said hormone-modulating active agent, the depot having a first, second and third orthogonal dimension, and wherein a length (h) of the polymeric matrix is longer than the longest dimension of the first, second and third orthogonal dimension; and the polymer matrix directly delivering said hormone-modulating active agent to said prostate in said subject as said hormone-modulating active agent diffuses through said plurality of surface areas of said polymer matrix when implanted in said prostate in said subject.

* * * * *

UNITED STATES PATENT AND TRADEMARK OFFICE
CERTIFICATE OF CORRECTION

PATENT NO. : 11,918,770 B2
APPLICATION NO. : 17/666138
DATED : March 5, 2024
INVENTOR(S) : Pamela Munster et al.

It is certified that error appears in the above-identified patent and that said Letters Patent is hereby corrected as shown below:

In the Specification

In Column 8, Line 28, delete "Tubing," and insert -- tubing, --.

In Column 8, Line 29, delete "Seen" and insert -- seen --.

In Column 8, Line 29, delete "Tubing" and insert -- tubing --.

In Column 11, Lines 14-15, delete "Tubing, Functioning" and insert -- tubing, functioning --.

In Column 11, Line 15, delete "Drug Eluting Delivery" and insert -- drug eluting delivery --.

In Column 13, Lines 36-37, delete "pentantoate" and insert -- pentanoate --.

In Column 13, Line 43, delete "poly(butylnethacrylate)," and insert -- poly(butylmethacrylate), --.

In Column 16, Line 23, delete "riamcinolone hexacatonide," and insert -- triamcinolone hexacetonide, --.

In Column 16, Line 44, delete "1-pyreecarbonate," and insert -- 1-pyrocarbonate, --.

In Column 27, Line 2, delete "Inguinal" and insert -- inguinal --.

Signed and Sealed this
Fourth Day of June, 2024

Katherine Kelly Vidal
*Director of the United States Patent and Trademark Office*